US008883723B2

(12) United States Patent
Doyle

(10) Patent No.: US 8,883,723 B2
(45) Date of Patent: Nov. 11, 2014

(54) CONJUGATE OF INSULIN AND VITAMIN B12 FOR ORAL DELIVERY

(75) Inventor: Robert Patrick Doyle, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 1003 days.

(21) Appl. No.: 12/074,641

(22) Filed: Mar. 4, 2008

(65) Prior Publication Data

US 2008/0242595 A1    Oct. 2, 2008

Related U.S. Application Data

(60) Provisional application No. 60/904,962, filed on Mar. 5, 2007.

(51) Int. Cl.
| | | |
|---|---|---|
| *A61K 38/28* | (2006.01) | |
| *A61K 38/02* | (2006.01) | |
| *A61K 38/16* | (2006.01) | |
| *A61P 3/10* | (2006.01) | |
| *A61K 47/48* | (2006.01) | |
| *A61K 38/26* | (2006.01) | |
| *A61K 38/22* | (2006.01) | |
| *A61K 38/17* | (2006.01) | |

(52) U.S. Cl.
CPC ........... *A61K 38/28* (2013.01); *A61K 47/48107* (2013.01); *A61K 38/26* (2013.01); *A61K 38/22* (2013.01); *A61K 38/1709* (2013.01); *A61K 38/2271* (2013.01)
USPC ............................................ 514/6.3; 514/5.9

(58) Field of Classification Search
None
See application file for complete search history.

(56) References Cited

U.S. PATENT DOCUMENTS

| | | | | |
|---|---|---|---|---|
| 5,428,023 A | | 6/1995 | Russell-Jones et al. | |
| 5,449,720 A | * | 9/1995 | Russell-Jones et al. | ..... 525/54.1 |
| 5,574,018 A | * | 11/1996 | Habberfield et al. | ........... 514/21 |
| 5,807,832 A | * | 9/1998 | Russell-Jones et al. | ........ 514/21 |
| 6,150,341 A | * | 11/2000 | Russell-Jones et al. | ........ 514/52 |
| 6,482,413 B1 | | 11/2002 | Chalasani et al. | |

FOREIGN PATENT DOCUMENTS

| | | |
|---|---|---|
| WO | WO 96/04016 | 2/1996 |
| WO | WO 98/08859 | 3/1998 |
| WO | WO 01/30967 | 5/2001 |
| WO | WO 02/074339 | 9/2002 |

OTHER PUBLICATIONS

Petrus et al. 'Vitamin B12 As Carrier for Oral Delivery of Insulin.' ChemMedChem. vol. 2, pp. 1717-1721. Dec. 2007.*
Huang et al. ("A novel insulin derivative chemically modified with dehydrocholic acid: synthesis, characterization and biological activity" Biotechnol. Appl. Biochem (2005) vol. 42: pp. 47-56).*
Russell-Jones, G.J., "Use of Vitamin $B_{12}$ Conjugates to Deliver Protein Drugs by the Oral Route," *Critical Reviews™ in Therapeutic Drug Carrier Systems*, vol. 15, No. 6, pp. 557-586, 1998.
Sundararajan, Chitra et al., "Synthesis and Characterization of Rhenium and Technetium-99m Labeled Insulin", *Journal of Medicinal Chemistry*, vol. 53, pp. 2612-2621 (2010).
Gliemann, J. et al., "The Biological Activity and the Binding Affinity of Modified Insulins Determined on Isolated Rat Fat Cells", *Diabetologia*, vol. 10, pp. 105-113 (1974). 1st page only.
Asada, H. et al., Abstract: "Stability of Acyl Derivatives of Insulin in the Small Intestine: Relative importance of Insulin Association Characteristics in Aqueous Solution", *Pharm Res.*, vol. 11(8), pp. 1115-1120 (1994). abstract only.
Doyle, Robert P., Reviewers' comments on NIH Grant Proposal (2007).

* cited by examiner

*Primary Examiner* — James H Alstrum Acevedo
*Assistant Examiner* — Tara Martinez
(74) *Attorney, Agent, or Firm* — Heslin Rothenberg Farley & Mesiti P.C.

(57) ABSTRACT

Compositions containing a therapeutic peptide covalently linked to Vitamin $B_{12}$ at the 5'-hydroxyl group of the ribose moiety of α-ligand are described. The length of the linkage is optimized so that the biological activity of both the Vitamin $B_{12}$ and the therapeutic peptide is maintained. Therapeutic peptide includes insulin, PYY, NPY and GLP-1. Attachment to Vitamin $B_{12}$ provides uptake of the therapeutic peptide from the digestive tract and longer residence time.

14 Claims, 22 Drawing Sheets
(7 of 22 Drawing Sheet(s) Filed in Color)

SEQUENCE LISTING

```
<160> NUMBER OF SEQ ID NOS: 4

<210> SEQ ID NO 1
<211> LENGTH: 90
<212> TYPE: PRT
<213> ORGANISM: Homo sapiens

<400> SEQUENCE: 1

Met Val Phe Val Arg Arg Pro Trp Pro Ala Leu Thr Thr Val Leu Leu
 1               5                  10                  15

Ala Leu Leu Val Cys Leu Gly Ala Leu Val Asp Ala Tyr Pro Ile Lys
            20                  25                  30
```

```
Pro Glu Ala Pro Gly Glu Asp Ala Ser Pro Glu Leu Asn Arg Tyr
            35                  40                  45

Tyr Ala Ser Leu Arg His Tyr Leu Asn Leu Val Thr Arg Gln Arg Tyr
 50                  55                  60

Gly Lys Arg Asp Gly Pro Asp Arg Leu Leu Ser Lys Thr Phe Phe Pro
 65                  70                  75                  80

Asp Gly Glu Asp Arg Pro Val Arg Ser Arg
                 85                  90

<210> SEQ ID NO 2
<211> LENGTH: 97
<212> TYPE: PRT
<213> ORGANISM: Homo sapiens

<400> SEQUENCE: 2

Met Val Phe Val Arg Arg Pro Trp Pro Ala Leu Thr Thr Val Leu Leu
 1               5                  10                  15

Ala Leu Leu Val Cys Leu Gly Ala Leu Val Asp Ala Tyr Pro Ile Lys
                20                  25                  30

Pro Glu Ala Pro Arg Glu Asp Ala Ser Pro Glu Glu Leu Asn Arg Tyr
            35                  40                  45

Tyr Ala Ser Leu Arg His Tyr Leu Asn Leu Val Thr Arg Gln Arg Tyr
 50                  55                  60

Gly Lys Arg Asp Gly Pro Asp Thr Leu Leu Ser Lys Thr Phe Phe Pro
 65                  70                  75                  80

Asp Gly Glu Asp Arg Pro Val Arg Ser Arg Ser Glu Gly Pro Asp Leu
                 85                  90                  95

Trp

<210> SEQ ID NO 3
<211> LENGTH: 97
<212> TYPE: PRT
<213> ORGANISM: Homo sapience

<400> SEQUENCE: 3

Met Leu Gly Asn Lys Arg Leu Gly Leu Ser Gly Leu Thr Leu Ala Leu
 1               5                  10                  15

Ser Leu Leu Val Cys Leu Gly Ala Leu Ala Glu Ala Tyr Pro Ser Lys
                20                  25                  30

Pro Asp Asn Pro Gly Glu Asp Ala Pro Ala Glu Asp Met Ala Arg Tyr
            35                  40                  45

Tyr Ser Ala Leu Arg His Tyr Ile Asn Leu Ile Thr Arg Gln Arg Tyr
 50                  55                  60

Gly Lys Arg Ser Ser Pro Glu Thr Leu Ile Ser Asp Leu Leu Met Arg
 65                  70                  75                  80

Glu Ser Thr Glu Asn Val Pro Arg Thr Arg Leu Glu Asp Pro Ala Met
                 85                  90                  95

Trp

<210> SEQ ID NO 4
<211> LENGTH: 30
<212> TYPE: PRT
<213> ORGANISM: Homo sapience

<400> SEQUENCE: 4

His Ala Glu Gly Thr Phe Thr Ser Asp Val Ser Ser Tyr Leu Glu Gly
 1               5                  10                  15
```

-continued

```
Gln Ala Ala Lys Glu Phe Ile Ala Trp Leu Val Lys Gly Arg
            20              25              30
```

US 8,883,723 B2

CONJUGATE OF INSULIN AND VITAMIN B12 FOR ORAL DELIVERY

RELATED APPLICATIONS

This application claims the benefit of U.S. Provisional application No. 60/904,962, filed Mar. 5, 2007, the entire disclosure of which is hereby expressly incorporated by reference.

BACKGROUND OF THE INVENTION

1. Field of the Invention

Embodiments of the invention relate to Vitamin $B_{12}$ conjugates for oral delivery of proteins and peptides, and more particularly, to Vitamin $B_{12}$ conjugated to insulin. Methods of preparing and using such conjugates in treatment of disease, particularly diabetes are described.

2. Description of the Related Art

Oral, enteric delivery of insulin is potentially an attractive means for non-invasive insulin delivery since it is likely to have high patient compliance. Previous research has demonstrated some promising results using the oral-enteric route but the bioavailability of only about 5% is low. Two major limitations related to successful oral-enteric delivery are proteolysis in the gastrointestinal tract and poor absorption from the intestine into the blood (Heinemann, L., et al., *Current Pharmaceutical Design* 2001, 7(14), 1327-1351; Shah, R. B., et al., *Critical Reviews in Therapeutic Drug Carrier Systems* 2002, 19(2), 135-169).

Specific uptake mechanisms exist in the gastrointestinal tract for uptake of dietary molecules. In the case of Vitamin $B_{12}$, a specific binding protein is released into the intestine which binds to its ligand in the lumen of the gut. Mammals have a transport mechanism for the absorption and cellular uptake of the relatively large Vitamin $B_{12}$ molecule which relies upon complexing to a naturally occurring transport protein known as Intrinsic Factor (*Chemistry and Biochemistry of B12*, Chapters 16 (Intrinsic Factor, Haptocorrin and their receptors) and 17 (Transcobalamin II), Banerjee, Ruma (Ed), Wiley Interscience 1999; Vitamin $B_{12}$ Zagalak, et al., (Eds), de Gruyter Press 1979). Russell-Jones et al. (U.S. Pat. Nos. 5,428,023 & 5,807,832) have shown that Vitamin $B_{12}$ can be coupled to a peptide, e.g., the D-Lys-6-analog of luteinizing hormone releasing hormone, so as to preserve the ability of Vitamin $B_{12}$ to interact with Intrinsic Factor, and thereby take advantage of the natural uptake mechanism for Vitamin $B_{12}$ to deliver the luteinizing hormone releasing hormone analog into the blood. Russell-Jones et al. teach attachment of the luteinizing hormone releasing hormone analog to Vitamin $B_{12}$ at a carboxyl group of an acid-hydrolyzed propionamide side chain (see FIG. 1).

Other proteins and peptides have also been conjugated to Vitamin $B_{12}$ in attempts to provide effective oral delivery compositions. For example, U.S. Pat. No. 5,574,018 teaches Vitamin $B_{12}$ conjugated to erythropoietin, granulocyte colony stimulating factor and consensus interferon through covalent binding at the primary hydroxyl site of the ribose moiety of the Vitamin $B_{12}$. Conjugates of other bioactive agents and Vitamin $B_{12}$ are taught by Grissom et al. (WO 01/30967 & WO 98/08859). Grissom et al. teach covalent attachment of cancer treatment drugs to the cobalt atom of Vitamin $B_{12}$. In some cases, see e.g., U.S. Pat. No. 6,482,413, the Vitamin $B_{12}$ is not directly linked to the target peptide or protein, but rather the Vitamin $B_{12}$ is linked to micro or nanocapsules containing unconjugated, intact peptide or protein. Although this approach is touted by the patentee as providing better protection against proteolysis and Vitamin $B_{12}$-mediated transport of larger payloads of biologically active peptide or protein, it presents many more technical issues related to polymer encapsulation technology and inefficient transport of the relatively large particles across the intestinal lining.

Despite the theoretical advantages of using a conjugate of Vitamin $B_{12}$ and insulin to provide an oral delivery form of insulin, no one has been successful in developing an effective conjugate. Indeed, researchers have concluded that it is not possible to link insulin to Vitamin $B_{12}$ such that the resulting conjugate is capable of ushering a therapeutically effective amount of biologically active insulin across the intestinal lining (see e.g., Table 1, Russell-Jones, G. J. 1998 *Crit. Rev. Ther. Drug Carrier Syst.* 15:557-586, indicating that Vitamin $B_{12}$ alone lacks the necessary capacity to transport insulin from the intestine into the blood).

Accordingly, there remains an important and unmet need for an oral delivery form of insulin, wherein adequate levels of active insulin are deliverable into the blood from the intestine using the Vitamin $B_{12}$-Intrinsic Factor uptake mechanism.

SUMMARY OF THE INVENTION

An oral delivery conjugate is disclosed in accordance with an aspect of the present invention. The conjugate comprises vitamin $B_{12}$ coupled to a therapeutically active polypeptide, wherein the polypeptide is covalently attached to a dicarboxylic acid derivative of the primary (5') hydroxyl group of the ribose moiety of vitamin $B_{12}$, and wherein the conjugate exhibits at least a portion of the therapeutic activity of the polypeptide.

In one embodiment, the therapeutically active polypeptide in the oral delivery conjugate is selected from the group consisting of insulin, protein YY (PYY), neuropeptide Y (NPY) and Glucagon-like peptide-1 (GLP-1). In a preferred embodiment, the therapeutically active polypeptide is insulin. The insulin preferably human and is coupled to the Vitamin $B_{12}$ at residues PheB1 or LysB29. However, insulins from other vertebrate species are also envisioned coupled to the $B_{12}$ vitamin. Such vertebrate include but not limited to bovine, ovine, equine, primate, canine, and feline.

In one embodiment of the oral delivery conjugate, the covalent attachment between the Vitamin $B_{12}$ and the polypeptide is through a linker. The linker may provide a carbamate-linked conjugate. In variations to this embodiment, the linker is selected from the group consisting of N,N'-carbonyldiimidazole (CDI), 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates. One preferred linker is N,N'-carbonyldiimidazole (CDI). In another variation, the linker may further comprise polyethylene glycol monomers.

A pharmaceutical composition is disclosed in accordance with another embodiment. The pharmaceutical composition comprises the above-described oral delivery conjugate and a pharmaceutically acceptable carrier. The composition may further comprise Intrinsic Factor, which is preferably a human Intrinsic Factor.

In accordance with another preferred embodiment, a pharmaceutical composition is described comprising an oral delivery form of insulin. The oral delivery form of insulin comprises vitamin $B_{12}$ covalently coupled to insulin, wherein the covalent coupling is between a dicarboxylic acid derivative of the primary (5') hydroxyl group of the ribose moiety of vitamin $B_{12}$ and residues PheB1 or LysB29 of insulin, wherein the covalent coupling optionally comprises a linker; and a pharmaceutically acceptable carrier suitable for oral delivery, wherein the pharmaceutical composition exhibits insulin-like activity when delivered orally to a mammal.

A method for treating diabetes mellitus is disclosed in accordance with another embodiment. The method comprises orally administering to a patient in need thereof an amount of the above-described pharmaceutical composition sufficient to lower blood glucose concentration in the patient, thereby treating the diabetes mellitus. Preferably, the pharmaceutical composition is in an oral delivery form selected from the group consisting of a capsule, a tablet, an emulsion, a colloidal dispersion, an elixir, a gel and a paste.

A kit is also disclosed in accordance with aspects of the invention. The kit comprises the above-described pharmaceutical composition and an instruction sheet for oral administration.

Further aspects, features and advantages of this invention will become apparent from the detailed description of the preferred embodiments which follow.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENT

Figure 1A:
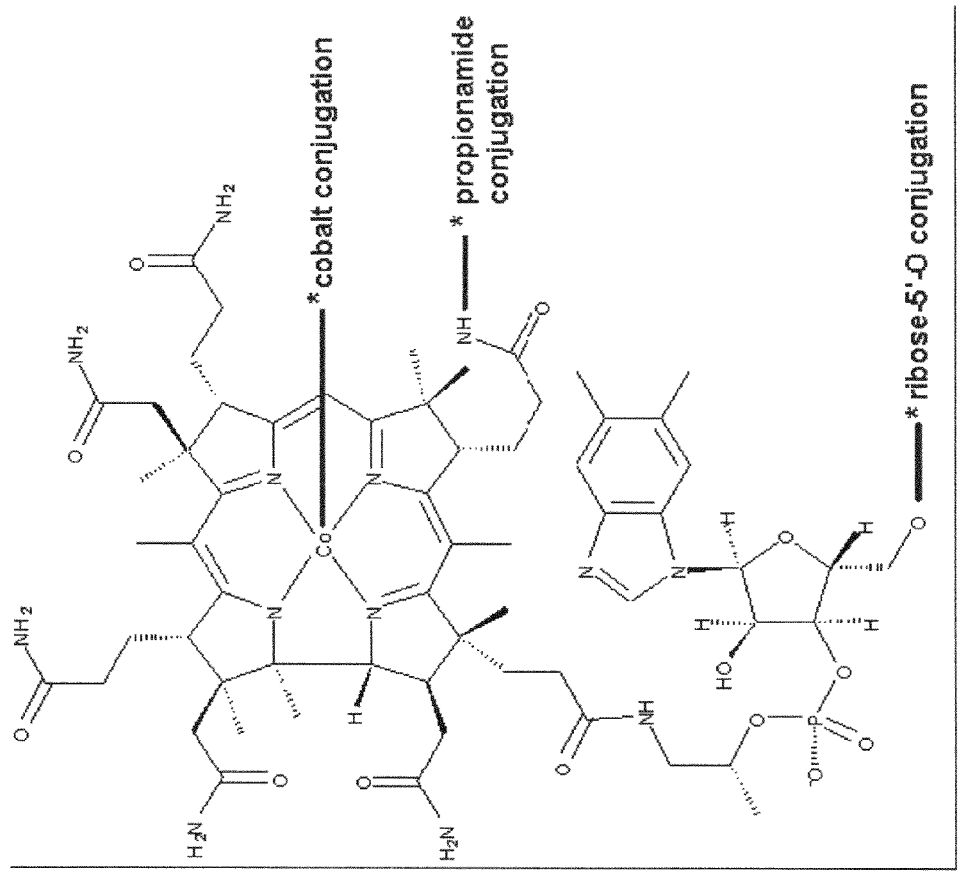
FIG. 1A. Structure of $B_{12}$ (cobalamin) with sites (indicated by an asterisk) that are modified by or for peptide attachment.

While the described embodiments represent the preferred embodiments of the present invention, it is to be understood that modifications will occur to those skilled in the art without departing from the spirit of the invention. The scope of the invention is therefore to be determined solely by the appended claims.

Definitions

Bioactive molecules or biologically active substances include proteins, peptides, hormones, small molecule drugs, haptens, antigens, antibodies.

Vitamin $B_{12}$ conjugate refers to the bioactive molecule or biologically active substance covalently linked to Vitamin $B_{12}$, either directly or through one or more linkers.

Bioactive Target Molecules for Conjugation to Vitamin $B_{12}$

Insulin

In accordance with a preferred embodiment of the invention, insulin is conjugated to Vitamin $B_{12}$. Since its isolation in 1922 by Banting and Best, insulin has been one of the most extensively studied molecules in biochemistry. Its primary structure (Sanger et al., 1955) and chemical synthesis (Meinenhofer et al., 1963) were the first established for a protein. Insulin is composed of 51 amino acids in two peptide chains (A and B) linked by two disulfide bonds. The three-dimensional structure of the insulin molecule (insulin monomer), essentially the same in solution and in solid phase, exists in two main conformations. These differ in the extent of helix in the B chain which is governed by the presence of phenol or its derivatives. In acid and neutral solutions, in concentrations relevant for pharmaceutical formulation, the insulin monomer assembles to dimers and at neutral pH, in the presence of zinc ions, further to hexamers. Many crystalline modifications of insulin have been identified but only those with the hexamer as the basic unit are utilized in preparations for therapy. The insulin hexamer forms a relatively stable unit but some flexibility remains within the individual molecules. The intrinsic flexibility at the ends of the B chain plays an important role in governing the physical and chemical stability of insulin. A variety of chemical changes of the primary structure (yielding insulin derivatives), and physical modifications of the secondary to quaternary structures (resulting in "denaturation," aggregation, and precipitation) are known to affect insulin and insulin preparations during storage and use. Chemical deterioration of insulin during storage of pharmaceutical preparations is mainly due to two categories of chemical reactions, hydrolysis and intermolecular transformation reactions leading to insulin HMWT products. The predominant hydrolysis reaction is deamidation of Asn residues which in acid solution takes place at residue A21, in neutral medium at residue B3.

Insulin is essential for the metabolic processing of carbohydrates, fat, and protein. The many insulin-like biological activities include reducing blood glucose levels by allowing glucose to enter muscle cells and by stimulating the conversion of glucose to glycogen (glycogenesis) as a carbohydrate store. Insulin also inhibits the release of stored glucose from liver glycogen (glycogenolysis) and slows the breakdown of fat to triglycerides, free fatty acids, and ketones. It also stimulates fat storage. Additionally, insulin inhibits the breakdown of protein and fat for glucose production (gluconeogenesis) in both liver and kidneys. Hyperglycemia results when insulin deficiency leads to uninhibited gluconeogenesis and prevents the use and storage of circulating glucose. The kidneys cannot reabsorb the excess glucose load, causing glycosuria, osmotic diuresis, thirst, and dehydration. Increased fat and protein breakdown leads to ketone production and weight loss.

Diabetes mellitus (DM) is a chronic metabolic disorder caused by an absolute or relative deficiency of insulin hormone. Insulin is produced by the beta cells of the islets of Langerhans located in the pancreas, and the absence, destruction, or other loss of these cells results in type 1 DM, or insulin-dependent diabetes mellitus (IDDM). Most children with diabetes have IDDM and a lifetime dependence on regular injections of exogenous insulin. Overall incidence is at least 15 cases per 100,000 individuals annually and probably increasing. An estimated 3 children out of 1000 develop IDDM by age 20 years. More than 700,000 Americans have type 1 DM.

Type 2 DM, or non-insulin-dependent diabetes mellitus (NIDDM) is a heterogeneous disorder. Most patients with NIDDM have insulin resistance, and their beta cells lack the ability to overcome this resistance. Although this form of diabetes was previously uncommon in children, in some, countries 20% or more of new patients with diabetes in childhood and adolescence have NIDDM, a change associated with increased rates of obesity. Other patients may have inherited disorders of insulin release leading to maturity onset diabetes of the young (MODY). Of the total incidence of diabetes in the U.S., NIDDM accounts for about 90%, whereas IDDM accounts for the remaining 10%.

Anti-Obesity Peptides

In accordance with another preferred embodiment of the invention, Vitamin $B_{12}$ may be conjugated to appetite-suppressing peptides to provide an effective oral delivery anti-obesity composition.

Obesity has reached pandemic proportions and is associated with increased morbidity and mortality (National Institutes of Health, "Clinical guidelines on the identification, evaluation, and treatment of overweight and obesity in adults: The evidence report 1998"; See WorldWide Web at nhlbi.nih.gov/guidelines/obesity/obgdlns.htm). Despite increasing public health education and initiatives, its prevalence continues to rise with over 60% of adults in the U.S. considered overweight or obese (Flegal, K. M. et al. 2002 *JAMA* 288: 1723-7). The increasing prevalence of obesity among children and adolescents is an additional concern (Hedley, A. A. et al. 2004 JAMA 291:2847-50) that suggests worsening obesity trends in the future (Bays, H. E. 2004 Obesity Res. 12:1197-211). The National Institutes of Health (NIH) has recommended a 10% weight-loss threshold for obesity treatment strategies as a general guideline (National Heart, Lung, and Blood Institute Obesity Education Initiative. "Clinical guidelines on the identification, evaluation, and treatment of overweight and obesity in adults: the evidence report." Bethesda, Md.: US Department of Health and Human Services, 1998) given that this moderate weight loss is associated with improved health including better cardiovascular risk profiles and reduced incidences of type 2 DM (National Institutes of Health, "Clinical guidelines on the identification, evaluation, and treatment of overweight and obesity in adults: The evidence report 1998"; Padwal, R. S. and S. R. Majumdar, 2007 *Lancet* 369:71-77, National Heart, Lung, and Blood Institute Obesity Education Initiative. "Clinical guidelines on the identification, evaluation, and treatment of overweight and obesity in adults: the evidence report." Bethesda, Md.: US Department of Health and Human Services. 1998).

Anti-obesity pharmacotherapy has become a commonly utilized and important treatment strategy for weight loss in the obese (Padwal, R. S. and S. R. Majumdar, 2007 *Lancet* 369:71-77, Bays, H. and C. Dujovne, 2002 *Expert Opin. Invest. Drugs* 11:1189-204, Bays, H. E. 2004 *Obesity Res.* 12:1197-211, Halford, J. C. 2001 *Current drug targets,* 2:353-70, Halford, J. C. and J. E. Blundell, 2000 Progress Drug Res. 54:25-58). For an anti-obesity drug to be successful, two key attributes must be realized (Padwal, R. S. and S. R. Majumdar, 2007 *Lancet* 369:71-77). First, it should cause sustained, clinically significant reductions in bodyweight and reduce obesity-related morbidity and mortality. Currently prescribed anti-obesity drugs produce average placebo-subtracted weight losses of less than 5% (Padwal, R. S. and S. R. Majumdar, 2007 *Lancet* 369:71-77) over the long-tem, which falls below the recommendation set forth by the NIH. As such, current pharmacotherapy treatment is perceived only as an adjunct treatment for the management of obesity and not as a stand-alone treatment (Irwin, N. P. L. et al. 2007 *J. Peptide Science* 13:400-5). Second, the benefit-risk ratio of the drug must be favorable. The track record for safety of anti-obesity drugs has historically been poor (Padwal, R. S. and S. R. Majumdar, 2007 *Lancet* 369:71-77, Bays, H. and C. Dujovne, 2002 *Expert Opin. Invest. Drugs* 11:1189-204, Bays, H. E. 2004 *Obesity Res.* 12:1197-211, Abenhaim, L. et al. 1996 *New England J. Med.* 335:609-16;-14) and serious side-effects continue to be associated with current anti-obesity treatments (Padwal, R. S. and S. R. Majumdar, 2007 *Lancet* 369: 71-77, Bays, H. and C. Dujovne, 2002 *Expert Opin. Invest. Drugs* 11:1189-204;, Bays, H. E. 2004 *Obesity Res.* 12:1197-211, Connolly, H. M. et al. 1997 *New England J. Med.* 337: 581-8; Arbeeny, C. M. 2004 *Obesity Res.* 12:1191-6). Given the above, it has been a therapeutic and research goal to develop safe and effective anti-obesity drugs (Bays, H. E. 2004 *Obesity Res.* 12:1197-211).

Some endogenously secreted peptides have recently been identified and targeted as potential anti-obesity agents as a result of their appetite suppressing effects (Padwal, R. S. and S. R. Majumdar, 2007 *Lancet* 369:71-77, Bays, H. E. 2004 *Obesity Res.* 12:1197-211, Perez-Tilve, D., et al. 2006 *Endocrine* 29:61-71; Moran, T. H., et al. 2005 *Am. J. Physiol. Regulatory, Integrative And Comparative Physiology* 288: R384-8; Morainigo, R. et al. 2006 *J. Clin. Endocrinol. Metab.* 91:1735-40; Huda, M. S. et al. 2006 *Obesity Reviews* 7:163-8). The peptides receiving the greatest attention include $PYY_{3-36}$ and GLP-1.

Peptide YY (PYY) is a 36 amino acid hormone (GenBank Accession Number CR542129.1, MVFVRRPWPALTTVL-LALLVCLGALVDAYPIKPEAPGEDASPE ELNRYYASL-RHYLNLVTRQRYGKRDGPDRLLSKTFFP-DGEDRPVRSR, SEQ ID NO: 1), which together with pancreatic polypeptide (PP) (GenBank Accession Number NM_002722, MAAARLCLSLLLLSTCVALLLQPLL-GAQGAPLEPVYPGDNATPEQMAQ YAADLRRYINML-TRPRYGKRHKEDTLAFSEWGSPHAAVPRELSPLDL SEQ ID NO: 2) and neuropeptide-Y (NPY) (GenBank Accession Number K01911.1, MLGNKRLGLSGLTLALSLLV-CLGALAEAYPSKPDNPGEDAPAEDMARYYSALRHYI NLITRQRYGKRSSPETLISDLLMREST-ENVPRTRLEDPAMW, SEQ ID NO: 3), belongs to the pancreatic polypeptide family (Boggiano, M. M., et al. 2005 *Obesity Rev.* 6:307-22). These peptides are structurally and biologically similar, but are synthesized and secreted from different sources (Cerdaa-Reverter, J. M. et al. 2000 *Biochem. Cell Biol.* 78:371-92; Gehlert, D. R. 1998 *Proc. Soc. Exp. Biol. Med.* 218:7-22). PYY is mainly present in the ileum and expressed by large intestine endocrine cells (Beottcher, G. et al. 1993 *Regulatory Peptides* 43:115-30, Ekblad, E. and F. Sundler, 2002 *Peptides* 23:251-61), where it is released in response to nutrient ingestion, proportional to the calories consumed (Adrian, T. E. et al. 1985 *Gastroenterology* 89:1070-7). The more abundant truncated form of PYY, namely $PYY_{3-36}$, has received the greatest attention due to its putative effects on appetite control (Boggiano, M. M. et al. 2005 *Obesity Rev.* 6:307-22).

While central administration of $PYY_{3-36}$ has been shown to increase food intake (Boggiano, M. M. et al. 2005 *Obesity Rev.* 6:307-22, Ashby, D. and S. R. Bloom 2007 *Peptides* 28:198-202) possibly via the activation of the lower affinity receptors $Y_1$ and $Y_5$ (Kanatani, A., et al. 2000 *Endocrinology* 141:1011-6), peripheral (or systemic) administration of $PYY_{3-36}$ has been shown to inhibit food intake in rodents (Batterham, R. L., et al. 2002 Nature 418:650-4, Halatchev, I. G., et al. 2004 *Endocrinology* 145:2585-90), primates (Moran, T. H. et al. 2005 *Am. J. Physiol.* 288:R384-8, Koegler, F. R. et al. 2005 *Diabetes* 54:3198-204) and humans (Batterham, R. L. et al. 2003 *New England J. Med.* 349:941-8; le Roux, C. W. et al. 2006 *Endocrinology* 147:3-8; Neary, N. M. et al. 2005 *Endocrinology* 146:5120-7). In rodents however, the robustness of the suppression of caloric intake following both acute and chronic peripheral administration of $PYY_{3-36}$ (Boggiano, M. M., et al. 2005 *Obesity Rev.* 6:307-22) has been questioned, since some groups have had difficulty in replicating the anorexigenic effects of peripheral $PYY_{3-36}$ administration (Boggiano, M. M., et al. 2005 *Obesity Rev.* 6:307-22, Tscheop, M., et al. 2004 *Nature* 430: p. 1 P following 165; discussion 2 p following 165). The reasons for this are unclear, but may involve the invasive nature of administration (daily injections) since stress may itself reduce NPY signaling (Ashby, D. and S. R. Bloom 2007 *Peptides* 28:198-202, Kim, R. et al. 2003 *Brain Res.* 983:201-8). In addition to appetite suppressing effects, $PYY_{3-36}$ has also been shown to improve glycemic control in rodent models of diabetes (Pittner, R. A. et al. 2004 *Int. J. Obesity Related Metab. Disorders* 28:963-71)

Administration of $PYY_{3-36}$ reduces appetite/hunger ratings and decreases food intake in normal-weight and obese subjects (Batterham, R. L. et al. 2003 *New England J. Med.* 349:941-8, le Roux, C. W. et al. 2006 *Endocrinology* 147:3-8). A relatively short-term (90 min) infusion of $PYY_{3-36}$ has also been shown to produce a more prolonged reduction of appetite and food intake in humans (Batterham, R. L. et al. 2003 *New England J. Med.* 349:941-8). Thus, in contrast to most gastrointestinal peptides that only inhibit short-term food intake, $PYY_{3-36}$ may function as a medium- to long-term regulator of energy intake rather than as a short-term satiety signal. That $PYY_{3-36}$ performs a significant role in the control of appetite in humans is supported by a number of observations. In disease states characterized by weight-loss, such as inflammatory bowel disease, tropical sprue and cardiac cachexia, $PYY_{3-36}$ levels are elevated (Adrian, T. E. et al. 1986 *Gastroenterol.* 90:379-84; El-Salhy, M. 1998 *Acta diabetologica* 35:194-8; le Roux, C. W. et al. 2005 *Proc. Nutrition Society* 64:213-6). Conversely, in obese humans, fasting plasma concentrations of $PYV_{3-36}$ are reduced and overweight subjects have a relative deficiency of postprandial $PYV_{3-36}$ release associated with reduced satiety (Batterham, R. L. et al. 2003 *New England J. Med.* 349:941-8). Intravenous infusion of $PYV_{3-36}$ at a rate of 0.8 pmol.kq$^{-1}$.min$^{-1}$ into lean humans increased mean plasma $PYV_{3-36}$ levels from 8.3 to 43.5 pM, and mimicked postprandial $PYV_{3-36}$ concentrations (Batterham, R. L., et al. 2002 Nature 418:650-4). Plasma $PYV_{3-36}$ returned to baseline concentrations within 30 minutes of the end of the infusion. Despite this, at a free-choice buffet meal 2 hours after the end of the infusion, there was a significant reduction in calorie intake of approximately 36%, with no effect on fluid intake or on gastric emptying as assessed by paracetamol absorption (Batterham, R. L. et al. 2002 Nature 418:650-4). It is important to note, that despite lower basal levels of $PYY_{3-36}$ in obese humans, obesity does not appear to be associated with resistance to the effects of $PYV_{3-36}$. Infusion of $PYV_{3-36}$ into a group of obese volunteers resulted in a comparable reduction in calorie intake when compared with lean controls (Batterham, R. L. et al. 2003 *New England J. Med.* 349:941-8). Moreover, PYY levels and postprandial rise are also restored in obese individuals who manage to lose weight (Roth, C. L. et al. 2005 *J. Clin. Endocrinol. Metab.* 90:6386-91) and who undergo gastric bypass surgery (Morainigo, R. et al. 2006 *J. Clin. Endocrinol. Metab.* 91:1735-40, le Roux, C. W. et al. 2006 *Annals*

Surg. 243:108-14). Finally, a recent study has demonstrated that reversible PEGylation of PYY$_{3-36}$ may prolong its inhibition of food intake via increasing its functional half-life by up to eight-times (Shechter, Y. et al. 2005 *FEBS Lett.* 579: 2439-44).

The mechanisms of action of PYY remain to be established (Ashby, D. and S. R. Bloom 2007 *Peptides* 28:198-202, Wynne, K. et al. 2005 *J. Endocrinol.* 184:291-318). Since the N-terminal of PYY allows it to cross the blood-brain barrier freely (Nonaka, N. et al. 2003 *J. Pharmacol. Exp. Ther.* 306: 948-53), it is postulated that the effect of peripheral administration of PYV$_{3-36}$ on appetite is mediated via the arcuate Y$_2$ receptor (Broberger, C. et al. 1997 *Neuroendocrinology* 66:393-408). This relatively simple arcuate nucleus (ARC) model of action, involving inhibition and activation of NPY and POMC neurons respectively, has however, more recently given way to a more complicated system likely involving vagal afferent signals (Ashby, D. and S. R. Bloom 2007 *Peptides* 28:198-202). In addition, the effects of PYY$_{3-36}$ on other circulating gut hormones (such as a decrease in circulating ghrelin levels (Batterham, R. L., et al. 2003 *New England J. Med.* 349:941-8)) cannot be precluded as concomitant appetite-suppressing mechanisms.

Glucagon-like peptide-1 (GLP-1) (GenBank Accession Number NM_002054.2, MKSIYFVAGLFVMLVQG-SWQRSLQDTEEKSRSFSASQADPLSDPDQ MNED-KRHSQGTFTSDYSKYLDSRRAQD-FVQWLMNTKRNRNNIAKRHDEFERHAEG TFTSDVSSYLEGQAAKEFIAWLVKGRGR-RDFPEEVAIVEELGRRHADGSFSDEMNTIL DNLAARDFINWLIQTKITDRK, SEQ ID NO: 4) is cleaved from preproglucagon as a 36- or 37-amino acid molecule within the intestine, where it is co-localized in the endocrine L-cells of the distal gut with PYY (Eissele, R. et al. 1992 *Eur. J. Clin. Invest.* 22:283-91, Wettergren, A. et al. 1997 *Scand. J. Gastroenterol.* 32:552-5). GLP-1 is highly conserved across a number of species, implying an important physiological role. Both the 36- and 37-amino acid peptide isoforms seem to possess similar biological activities and roles, although GLP-1 (7-36) amide is present in greater quantities within the circulation and demonstrates a greater postprandial rise (Orskov, C. et al. 1994 *Diabetes* 43:535-9).

The action of GLP-1$_{(7-36)amide}$ that has attracted most attention, both from a physiological and a therapeutic viewpoint, is its potent incretin effect (Neaslund, E. et al. 2004 *British J. Nutrition* 91:439-46). The peptide mediates glucose-dependent insulinotropic effects in a number of species, including man (Kreymann, B. et al. 1987 *Lancet* 2:1300-4). GLP-1$_{(7-36)amide}$ also inhibits gastric acid secretion and gastric emptying, as well as suppressing glucagon release (therefore reducing hepatic-derived glucose) and promoting an increase in pancreatic β-cell mass (Tolessa, T. et al. 1998 *Digestive Dis. Sci.* 43:2284-90; Tolessa, T. et al. 1998 *J. Clin. Invest.* 102:764-74; Edvell, A. and P. Lindstreom 1999 *Endocrinol.* 140:778-83). As a therapeutic target, there has been substantial interest in GLP-1, since actions of GLP-1 (inhibition of gastric emptying; decreased blood glucose concentration) are preserved in subjects with poorly controlled Type 2 Diabetes (Nauck, M. A. et al. 1993 *J. Clin. Invest.* 91:301-7; Willms, B. et al. 1996 *J. Clinical Endocrinol. Metab.* 81:327-32).

Indeed, EXENATIDE (Byetta; FDA approved for treatment of type 2 diabetes) is a potent agonist for the mammalian GLP-1 receptor, and thus displays similar functional properties to native GLP-1, has been assessed as a treatment for Type 2 diabetes in three Phase 3 clinical trials (the AMIGO studies). Among many positive effects of Exenatide to date, are included; glucose lowering and insulin sensitizing effects in diabetic mice, rats and monkeys (Young, A. A. et al. 1999 *Diabetes* 48:1026-34); beta-cell replication and neogenesis resulting in improved glucose tolerance in diabetic rats (Xu, G. et al. 1999 *Diabetes* 48:2270-6) as well as streptozotocin-treated newborn rats (Tourrel, C. et al. 2001 *Diabetes* 50:1562-70); and decelerated weight gain and fat deposition in Zucker rats (Szayna, M. et al. 2000 *Endocrinol.* 141:1936-41). Consistent with its role as an incretin, GLP-1$_{(7-36)amide}$ is released into the circulation in response to a meal and in proportion to the calories ingested (Orskov, C. et al. 1994 *Diabetes* 43:535-9, Kreymann, B. et al. 1987 *Lancet* 2:1300-4).

Both CNS-injected and peripherally administered GLP-1$_{(7-36)amide}$ inhibit food intake in a number of species wherein the site of action appears to be the brainstem -hypothalamus axis (Turton, M. D. et al. 1996 *Nature* 379:69-72). GLP-1$_{(736)amide}$ dose-dependently decreases appetite and caloric intake in lean and obese humans and patients with diabetes (Gutzwiller, J. P. et al. 2004 *Physiology & behavior* 82:17-9; Gutzwiller, J. P. et al. 1999 *Am. J. Physiol.* 276: R1541-4; Neaslund, E. et al. 1999 *Int. J. Obesity And Related Metabolic Disorders* 23:304-11). In a recent meta-analysis, it was concluded that infusion of GLP-1$_{(7-36)amide}$ reduces both appetite and food intake, the latter by an average of 11.7% acutely (Verdich, C. et al. 2001 *J. Clin. Endocrinol. Metab.* 86:4382-9). The magnitude of this reduction is similar in lean and obese men. Prandial subcutaneous injections of GLP-1$_{(7-36)amide}$ given to obese but otherwise healthy subjects for 5 days resulted in a weight loss of 0.55 kg (Neaslund, E. et al. 2004 *British J. Nutrition* 91:439-46). One potential barrier to the use of native GLP-1$_{(7-36)amide}$ in a clinical setting is its short half-life (approximately 2 min). Since reversible PEGylation has previously been shown to increase the functional half-life of PYY$_{3-36}$ by up to eight-times (Shechter, Y. et al. 2005 *FEBS Lett.* 579:2439-44), the effect of conjugating at position 1 of GLP-1$_{(7-36)amide}$ (enzyme dipeptidyl peptidase IV degrades GLP-1 at the alanine located at position 2; see Methods section for further information), also is envisioned to result in extended in vivo activity of GLP-1. Indeed, a GLP-1 receptor agonist (GLP-1/glucagon hybrid peptide) has recently been PEGylated (see methods section) which resulted in a dramatically prolonged activity in vivo (Claus, T. R. et al. 2007 *J. Endocrinol.* 192: 371-80).

While the paraventricular nucleus of the hypothalamus was the initial focus of studies linking GLP-1 actions to satiety, several studies have now demonstrated, using direct injection approaches that multiple brain regions are capable of eliciting a CNS satiety effect in response to GLP-1, including the lateral, dorsomedial, and ventromedial hypothalamus, but not the medial nucleus of the amygdala (Schick, R R et al. 2003 *Am. J. Physiol. Regulatory, Integrative And Comparative Physiol.* 284:R1427-35; Alpers, D. and G. Russell-Jones in: *Chemistry and Biochemistry of B$_{12}$*, R Banerjee, Editor. 1999, Wiley Interscience). The mechanisms transducing the anorectic actions of GLP-1R agonists appear to overlap with those activated by PYY$_{3-36}$, but distinct pathways are identified for these peptides since additive effects are observed with co-administration (Neary, N. M., et al. 2005 *Endocrinology* 146:5120-7).

In summary, PYY$_{3-36}$ and GLP-1$_{7-36}$ are endogenously occurring peptides that in addition to improving glycemic control, have also been identified as having appetite suppressing effects. Furthermore, previous research investigating the concurrent administration of these peptides has identified an additive effect of these peptides on appetite suppression (Neary, N. M. et al. 2005 *Endocrinol.* 146:5120-7). Finally, both of these peptides have previously been conjugated, wherein their potency remained unaffected. Current anti-obesity pharmacotherapy is aimed, among other things, at stimulating the release of these peptides or at mimicking these peptides' appetite suppressing response. We envision that by using the naturally occurring $B_{12}$ uptake pathway that we develop an oral administration route for these peptides. This is examined using the same principles and techniques that enabled the successful delivery of orally administered insulin (as described below).

Vitamin $B_{12}$ Conjugates

Embodiments of the invention are directed to complexes which include a bioactive substance linked to at least one carrier molecule which is Vitamin $B_{12}$ or an adenosylcobalamin, methylcobalamin, cyanocobalamin, aquocobalamin, glutathionylcobalamin, hydroxycobalamin, cyanocobalamin carbanalide, and 5-o-methylbenzylcobalmin ((5-OMeBza) CN-Cbl), as well as the desdimethyl, monoethylamide and the methylamide analogs of all of the above. Also included are the various analogs and homologs of cobalamin such as coenzyme Vitamin $B_{12}$ and 5'-deoxyadenosylcobalamin. Other analogs include chlorocobalamin, sulfitocobalamin, nitrocobalamin, thiocyanatocobalamin, benzimidazole derivatives such as 5,6-dichlorobenzimidazole, 5-hydroxybenzimidazole, trimethylbenzimidazole, as well as adenosylcyanocobalamin ((Ade)CN-Cbl), cobalamin lactone, cobalamin lactam and the anilide, ethylamide, monocarboxylic and dicarboxylic acid derivatives of Vitamin $B_{12}$ or its analogs. Both the ability of the Vitamin $B_{12}$ portion of the conjugate to undergo binding reactions for uptake and transport in a vertebrate host and the activity of the biologically active substance are substantially maintained.

Preferred embodiments of the invention are directed to biologically active substances, such as proteins and peptides, covalently linked to Vitamin $B_{12}$. The biologically active substance-Vitamin $B_{12}$ conjugate has the advantage that biologically active substance may be administered orally rather than by intravenous injection. It avoids the side effects of other non-invasive routes of administration, such as nasal or pulmonary administration. Administration of the biologically active substance-Vitamin $B_{12}$ conjugate has the further advantage that a necessary vitamin is co-administered. The biologically active substance-Vitamin $B_{12}$ conjugate has a long-lived mode of action which is a further advantage, regardless of how the conjugate is administered.

Preferred derivatives of Vitamin $B_{12}$ include the mono-, di- and tricarboxylic acid derivatives or the proprionamide derivatives of Vitamin $B_{12}$. Carriers may also include analogs of Vitamin $B_{12}$ in which the cobalt is replaced by zinc or nickel. The corrin ring of Vitamin $B_{12}$ or its analogs may also be substituted with any substituent which does not affect its binding to Intrinsic Factor.

In a preferred embodiment of the invention there is provided a covalently linked conjugate comprising a Vitamin $B_{12}$ covalently linked to peptide, in particular, the peptide is selected from insulin, insulin analogs, PYY and analogs thereof such as $PYY_{3-36}$, GLP-1 and cholecystokinin (CCK) peptides, particularly, CCK-8 peptides. More preferably, the peptide is selected from insulin, insulin peptide fragments, insulin peptide precursors, insulin-like growth factors, or insulin analogs. The peptides are preferably from mammalian sources, more preferably human sources.

Figure 1B:
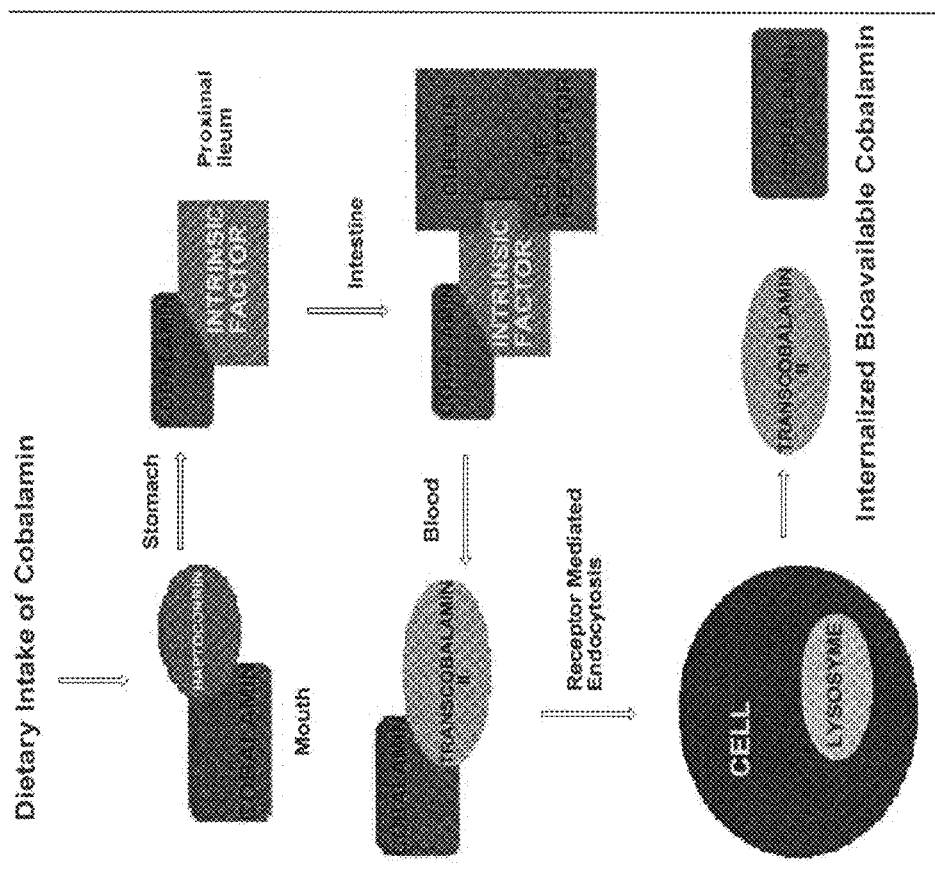
FIG. 1B. Dietary uptake of $B_{12}$.

Mammals have an active transport mechanism in the GIT for the absorption and cellular uptake of the relatively large Vitamin $B_{12}$ molecule (~1350 Da; see FIG. 1). Embodiments of the delivery system take advantage of the natural Intrinsic Factor mediated uptake mechanism for dietary Vitamin $B_{12}$ (see FIG. 1) to overcome the two major hurdles of enteric delivery, namely protection of biologically active substance from GIT proteolysis and uptake and transcytoses of the enterocyte.

Vitamin $B_{12}$ first binds to haptocorrin, a salivary enzyme that protects and transports Vitamin $B_{12}$ through the stomach and into the small intestine. The Vitamin $B_{12}$ then binds to Intrinsic Factor and proceeds down the small intestine where the complex binds to the IF-receptor on the ileum wall. The Intrinsic Factor-Vitamin $B_{12}$ receptor complex then undergoes endocytosis, releasing Vitamin $B_{12}$ into the blood serum where it becomes bound to transcobalamin (II) (TCII). Embodiments of the invention adapt this uptake pathway for the delivery of a biologically active substance, such as a biologically active protein. The recognition of, and affinity for, the various binding Vitamin $B_{12}$ proteins is maintained. Conjugation to Vitamin $B_{12}$ protects bound proteins from digestion and also facilitates their internalization and transport into blood serum overcoming the two major hurdles for oral delivery of biologically active substances. In people with impaired Vitamin $B_{12}$ uptake, research has shown that co-administration of Intrinsic Factor alongside Vitamin $B_{12}$ greatly increases uptake (WO 03/026674).

In some preferred embodiments, Intrinsic Factor is co-administered along with the Vitamin $B_{12}$ conjugate to increase uptake of the Vitamin $B_{12}$-biologically active substance conjugate.

Embodiments of the invention include Vitamin $B_{12}$ conjugates that can be used to deliver a biologically active substance to any uni- or multicellular organism with a requirement for and a specific transport mechanism for Vitamin $B_{12}$.

Vitamin $B_{12}$ also undergoes what is termed "enterohepatic recirculation" from bile salts (*Chemistry and Biochemistry of $B_{12}$*, Chapter 15, pages 406-407, Banerjee, Ruma (Ed), Wiley Interscience 1999). This "recycling" of Vitamin $B_{12}$ is vital in ensuring Vitamin $B_{12}$ deficiency does not occur. By coupling biologically active substance to Vitamin $B_{12}$, this recirculation will result in a longer mean residency time for biologically active substance, essentially producing a long-acting biologically active substance. The "side product" of this process will be a dose of Vitamin $B_{12}$. In preferred embodiments, the biologically active substance is insulin and coupling to Vitamin $B_{12}$ results in a longer mean residency time compared to unconjugated insulin. Since many people with Diabetes Mellitus are Vitamin $B_{12}$ deficient, administration of Vitamin $B_{12}$ is an additional benefit to this approach.

The major advantages of this system then are (1) oral delivery, (2) the potential to increase uptake or tailor uptake with Intrinsic Factor co-administration, (3) no catalytic additives being required for the absorption of biologically active substance (instead a necessary vitamin is administered) and (4) enterohepatic recirculation for extended residence times in vivo. These points will make this system suitable as a basal therapy that will have high patient compliance. Preferred embodiments are directed to a basal therapy to be administered once or twice daily (total duration of action being 24 hrs, minimal "peak" in activity).

Both the attachment point on the protein and the attachment point on the Vitamin $B_{12}$ must be carefully considered. Attachment cannot be anywhere on the biologically active substance molecule without loss of activity or compromising stability. Attachment of the Vitamin $B_{12}$ to the protein potentially affects the three dimensional structure which in turn may affect biologically active substance effectiveness and stability.

In preferred embodiments, the Vitamin $B_{12}$ and biologically active substance are coupled together in such a way that neither molecule is inhibited by the other. Preferably, the vitamin is recognized by the series of enzymes involved in its uptake through the GIT so that the biologically active substance interacts with its receptor to induce the cascade effect. In preferred embodiments, specific sites on both molecules are chosen for conjugation, wherein the sites are known not to be important for recognition and activity. In some embodiments, the Vitamin $B_{12}$ and biologically active substance will be coupled directly together. In more preferred embodiments, Vitamin $B_{12}$ and the bioactive molecule are coupled with a linker. More preferably, the Vitamin $B_{12}$ and biologically active substance are held apart by "spacer" units to produce distance between the Vitamin $B_{12}$ and biologically active substance.

In some embodiments, the spacer units are provided by polyethylene glycol (PEG) monomers. In some embodiments, the mean residence time of the biologically active substance is increased by the use of long chain polyethylene glycol (PEG) units (750-10000 Da). Conjugates of the type Vitamin $B_{12}$-$PEG_{750-10000}$-biologically active substance are produced.

It has been extensively reported in the literature that PEG conjugates exhibit increased plasma half-lives, improved resistance to proteolysis, reduced immunogenicity and antigenicity compared to parental compounds including proteins (Van Spriel, A. B. et al. 2000 *Cytokine* 12:666-670; Park, Y. et al. 2002 *Bioconjugate Chemistry* 13:232-239; Werle, M. et al. 2006 *Amino Acids* 30:351-367; Pasut, Gianfranco et al. *Adv. Polymer Sci.* 192:95-134).

In some embodiments, the conjugates are coupled through bifunctional PEG units with a stable bond at the biologically active substance-PEG junction but a reversible bond at the Vitamin $B_{12}$-PEG junction (e.g., a disulfide bond sensitive to reducing agents in blood serum) to achieve targeted release. This approach provides a longer-lived biologically active substance (compared to non-PEGylated forms), which is transported orally. Besides providing for optimization of the spacing between the Vitamin $B_{12}$ and the biologically active molecule, the PEG linkers provide better uptake and longer lifetime for the biologically active substance.

There are three potential attachment sites on the Vitamin $B_{12}$ molecule as shown in FIG. 1A. Stability of the attached protein must be maximized and the protein must maintain at least a substantial portion of activity after attachment. Preferably, at least 20% of the activity is maintained after attachment to Vitamin $B_{12}$, more preferably at least 30%, yet more preferably at least 40%, yet more preferably at least 50%, yet more preferably at least 60%, yet more preferably at least 70%, yet more preferably at least 80%, yet more preferably at least 90%, yet more preferably at least 95% and most preferably 100% activity compared to the native protein.

In some embodiments, there is no linker and attachment is directly between Vitamin $B_{12}$ and biologically active substance. In preferred embodiments, a linker is used. The linker may be of various lengths. In preferred embodiments, the linker may be about 3-150 atoms in length, more preferably about 3-100 atoms in length, and most preferably about 3-40 atoms in length. In general, longer linkers improve stability and function as they allow for some distance of the peptide or protein from Vitamin $B_{12}$ and proper folding of the protein portion of the conjugate. Preferred linkers include carbamate-based linkers assembled using a N,N'-carbonyldiimidazole (CDI). A non-limiting list of suitable coupling agents also include 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

As discussed above, in some embodiments one or more PEG monomers are added to optimize the distance between the Vitamin $B_{12}$ and the biologically active substance.

The some embodiments, the linker may be degradable. The degradation may occur naturally in the body or require the administration of a second factor to trigger degradation of the linker and release of free biologically active substance from the Vitamin $B_{12}$-biologically active substance complex. Examples of such degradable linkers include disulfide bonds, thioesters, esters, carbamates, and thioethers.

Conjugation of insulin may take place on the Vitamin $B_{12}$ at one of three major sites (see FIG. 1A): (1) the cobalamin's $\beta$ axial site at the cobalt atom; (2) direct conjugation of insulin to the peripheral corrin ring propionamide units (there are three but the $\epsilon$-position avoids Intrinsic Factor uptake interference); and (3) through the 5'-hydroxy group of the ribose unit of the $\alpha$ "tail" of Vitamin $B_{12}$. In preferred embodiments, conjugation of Vitamin B12 to the biologically active material is at site no. (3), that is, at the 5'-hydroxy group of the ribose unit of the a unit.

In some embodiments, the Vitamin $B_{12}$-conjugated biologically active substance may be encapsulated in protective liposomes for greater improvement in stability.

Embodiments of the invention provide for extended release by enterohepatic recirculation of Vitamin B12.

Synthesis of Vitamin $B_{12}$-Insulin Conjugates

Insulin and Vitamin $B_{12}$ are coupled either directly or through short to long chain linkers. The system allows the Vitamin $B_{12}$ uptake pathway to protect insulin from digestion and deliver it to blood serum but does not interfere with insulin's activity. Three possible sites on Vitamin B12 for attachment are shown in FIG. 1A. These are cobalt conjugation, propionamide conjugation, and ribose-5'-O conjugation. In preferred embodiments, insulin is attached at the OH of the ribose ring. Various sites on insulin may provide suitable coupling locations. The link between Vitamin $B_{12}$ and insulin may also be varied to optimize activity. Varying linker lengths may play a role in the balance between successful uptake and suitable activity. PEG monomers are useful to optimize the length of the linker sequence.

Embodiments of the invention are directed to synthesized complexes of the type Vitamin $B_{12}$-Insulin directly conjugated or Vitamin $B_{12}$-spacer-Insulin. In preferred embodiments, the "spacer" groups between the insulin and Vitamin $B_{12}$ are short bifunctional alkyl chains of varying lengths (typically 3-40 atoms) which facilitate both the conjugation of Vitamin $B_{12}$ and insulin and provide varying degrees of separation between the two. In this embodiment, the Vitamin $B_{12}$ and insulin are coupled irreversibly. However, degradable linkers may also be used.

In preferred embodiments, conjugation to both bovine and human insulin is achieved by covalently linking Vitamin $B_{12}$ or Vitamin $B_{12}$-spacers (3-40 atoms) to the PheB1 or LysB29 residues. It has been determined previously that these amino acids do not participate in receptor binding and mutation does interfere with insulin activity in vivo (Hinds, K, et al. 2000 *Bioconjugate Chem.* 11:195-201). In a most preferred embodiment, the prepared conjugate has been based on the LysB29. In some embodiments, a protecting group is applied for protection of insulin's terminal amines, as when coupling to LysB29. This can be readily achieved using dimethyl maleic anhydride coupled specifically at pH 6.8-6.9. Irreversible conjugation itself may be achieved using organic chemistry/conjugate chemistry techniques as appropriate.

In an alternate preferred embodiment, insulin is reversibly coupled to Vitamin $B_{12}$. In this embodiment, the Vitamin $B_{12}$ facilitates insulin's enteric transport and uptake, but then the insulin is released once the conjugate arrives in the blood. Greater spacing between the sterically bulky insulin and Vitamin $B_{12}$ may also offer greater IF binding to increase conjugate efficacy. This embodiment provides an oral delivery route for insulin, but rules out extended presence of active insulin through Vitamin $B_{12}$ dependent enterohepatic circulation.

In some embodiments, insulin mean residence time is increased by the use of long chain polyethylene glycol (PEG) units (750-10000 Da). Conjugates of the type Vitamin $B_{12}$-$PEG_{750-1000}$-Insulin are produced as discussed generally above.

In some embodiments, the conjugates are coupled through bifunctional PEG units with a stable bond at the insulin-PEG junction but a reversible bond at the Vitamin $B_{12}$-PEG junction (e.g., a disulfide bond sensitive to reducing agents in blood serum) to achieve targeted release. This approach provides a longer-lived insulin (compared to non-PEGylated forms) which is transported orally.

As will be apparent to those skilled in the art, the strategies discussed above can be combined to produce an insulin-Vitamin $B_{12}$ conjugate with the desired properties. Combined, the two approaches involving short or long chain spacers, reversibly or irreversibly coupled, offer an extensive ability to diversify and optimize the system to produce the desired uptake, activity and longevity.

Superior convenience compared to intravenous administration leads to high patient compliance. Embodiments of the invention provide a biologically active substance that meets the requirements of a sustained basal insulin level for people with diabetes by utilizing the natural dietary uptake pathway of Vitamin $B_{12}$.

Biological and In Vivo Uptake Studies with Successfully Screened Conjugates

Insulin folding studies and insulin receptor binding assays confirm active insulin is present while bound to Vitamin $B_{12}$. The insulin may be modified at the N-terminus of the B chain with a fluorescent tag. It has been demonstrated that modification at this position does not greatly affect biological activity or standard insulin assays (≥70% activity relative to natural insulin has been observed) (WO 02/36169.; Kaneda, Norio, et al. 1983 *J. Biochem.* 94:1317-28). This fluorescent tag (fluorescein) may be used to facilitate the study of conjugate binding to the insulin-receptor as well as insulin-binding assays followed by fluorescence polarization and/or flow cytometry techniques.

Experiments are conducted in streptozotocin (STZ)-treated rats to determine the uptake kinetics and efficiency of the Vitamin $B_{12}$-insulin systems. The end-points to be assessed are blood insulin and glucose concentration.

The successful uptake of the synthesized Vitamin $B_{12}$-insulin conjugates prepared according to embodiments of the invention is assessed. The biological efficiency of this delivery system is determined by monitoring acute changes in blood glucose and insulin concentration. In preferred embodiments, an animal model is used, most preferably, the streptozotocin (STZ)-treated rat, a model of type 1 diabetes.

In some embodiments, the STZ is administered through a cannula inserted in the jugular vein. Since blood glucose concentrations will be elevated in this model, a change in the blood glucose concentration is indicative that the oral-insulin delivery was successful and will provide a means for measuring the biological efficiency. In preferred embodiments, assays for the presence and quantification of insulin and C-Peptide (DPC) in plasma are conducted to support the observed changes in blood glucose.

The $B_{12}$-insulin conjugate binding to the insulin receptor is assessed using $P^{31}$ NMR by following phosphorylation of the insulin receptors tyrosine residues.

Synthesis of Other Vitamin $B_{12}$-Peptide Conjugates

Vitamin $B_{12}$ is coupled, both reversibly and irreversibly, through short to long chain linkers to peptide YY ($PYY_{3-36}$) or glucagon-like peptide-1 ($GLP-1_{(7-37amide)}$). We build and optimize a system that allows the $B_{12}$ uptake pathway to protect these peptides from digestion and deliver them to blood serum and subsequently to the brain without diminishing their activity. To achieve this, a number of suitable coupling locations on both $B_{12}$ and the particular peptide are explored. The link between $B_{12}$ and the particular peptide is also varied to optimize activity. Varying linker lengths play an important role in the balance between successful uptake and suitable activity.

Chemical and Biochemical Characterization of the Vitamin $B_{12}$ Peptide Conjugates We validate that the $B_{12}$-peptide conjugates are successfully synthesized including that conjugation has occurred at the desired coupling sites. Protein folding studies (circular dichroism and nuclear magnetic resonance) and receptor binding assays (e.g. TCII receptor) provide information on structure and confirm in vitro activity of each particular conjugate. Binding assays for $B_{12}$ uptake proteins (Intrinsic Factor) and transcobalamin (TCII)) are conducted to ensure the enzymes involved in the $B_{12}$ transport pathway still recognize $B_{12}$ and are not inhibited by the presence of each peptide. Receptor binding experiments for PYY and GLP-1 are conducted. Experiments to gauge whether conjugation provides greater stability to gastrointestinal enzymes are also conducted.

Biological and in vivo Uptake Studies with Successfully Screened Conjugates

To assess bioavailability of the conjugates characterized in the study above, both uptake studies and short-term (5 hours) feeding studies are conducted using Sprague-Dawley (SD) rats and diet induced obese SD (DIOSD) rats. The uptake studies assess the extent to which peptides appear in the systemic circulation by measuring their concentration (RIA) in response to conjugate administration by oral gavage. The short-term feeding studies assess alterations in food and water intake (five hours post administration) in response to conjugate administration by oral gavage. Oral gavage is performed during the conscious state.

The present invention enables the delivery of $PYY_{3-36}$ and GLP-1 into the systemic circulatory system following their oral administration, using the Vitamin $B_{12}$ uptake pathway, wherein the $PYY_{3-36}$ and GLP-1 both retain their biological activity.

This invention has direct relevance to the development of anti-obesity drug treatments that will be associated with; (1)

high efficacy rates due to their appetite-suppressing effects and concomitant benefits to obesity-related disease; (2) high rates of compliance due to their mode of administration (orally); (3) high benefit-risk ratios due to the combination of endogenously released compounds and vitamin $B_{12}$. Each point is developed further below:

High Rates of Compliance Due to Their Mode of Administration (Orally)

To adapt this uptake pathway for neuro-peptide delivery, the recognition of, and affinity for, the various binding $B_{12}$ proteins must not be lost or grossly diminished. Using insulin as the lead compound, we synthesized and demonstrated, both in vitro and in vivo, the successful conjugation of a peptide hormone to $B_{12}$ (see Examples). Conjugation to $B_{12}$ then both protects bound proteins from digestion and also facilitates their internalization and transport into blood serum overcoming the two major hurdles for oral peptide delivery mentioned earlier. Given that brain delivery is required for the function of neuro-peptides such as PYY it is important to note that vitamin $B_{12}$ can cross the blood brain barrier in a process believed to be mediated by TCII (Hansen, M. and E. Nex 1987 *Biochim. Biophys. Acta* 926:359-64; Lazar, G. S. and R Carmel 1981 *J. Lab. Clin. Med.* 97:123-33; Zetterberg, H. et al. 2003 *Clinical Chem.* 49:1195-8). In people with impaired or inefficient $B_{12}$ uptake, the co-administration of IF with $B_{12}$ may enhance the GIT uptake process (Alpers, D. and G. Russell-Jones in: *Chemistry and Biochemistry of $B_{12}$*, R Banerjee, Editor. 1999, Wiley Interscience).

Reabsorption may also be achieved by maintaining high affinity for IF. Due to the physiological importance of $B_{12}$, after being secreted into bile, $B_{12}$ may be reabsorbed through a highly efficient enterohepatic recirculation pathway. This implies that each peptide, when bound irreversibly to $B_{12}$, may be recirculated allowing for extended therapeutic activity (longer mean residency time) akin to the use of PEGylation technologies with $PYY_{3-36}$ (Shechter, Y. et al. 2005 *FEBS Lett.* 579:2439-44).

A critical component to the success of this delivery strategy is that the uptake capacity of the $B_{12}$ pathway is sufficient to meet the necessary increase in plasma $PYY_{3-36}$ and $GLP-1_{(7-36)amide}$ levels required to suppress appetite. Using the $B_{12}$ uptake pathway, it is expected that we will be able to deliver 1.1 nmoles of peptide per dose into the systemic circulation (at an efficiency of 25%) (*Vitamin $B_{12}$, in Dietary Reference Intakes for Thiamin, Riboflavin, Niacin, Vitamin B6, Folate, Vitamin $B_{12}$, Pantothenic Acid, Biotin, and Choline* 1998, (Institute of Medicine) The National Academies Press. p. 306-308). Given that IF-mediated endocytosis via Cubulin is the limiting step in this process, it is important to note that Cubulin recycles every 30 min (Bose, S. et al. 1997 *J. Biol. Chem.* 272:3538-43) and as such, multiple dosing (e.g., every 45 min) may be adopted to increase the quantity of peptide absorbed (Alsenz, L. et al. 2000 *Pharmaceutical Res.* 17:825-32). This recycling may also be important, when considering dietary $B_{12}$ competition.

With respect to $PYY_{3-36}$, obese and lean subjects receiving a total dose of 2 nmol/m² of body-surface area during a 90-min infusion period, decreased their caloric intake by 30% and 31% respectively (Batterham, R. L., et al. 2003 *New England J. Med.* 349:941-8). With respect to GLP-1, intravenous infusions of GLP-1 (72 pmol.h$^{-1}$) for 390 min, reduced the rise in ghrelin levels in the late postprandial period and it is this suppression of ghrelin that may be involved in GLP-1's anorexic effects (Hagemann, D. et al. 2007 *Regulatory peptides* 143:64-8). These studies indicate that the anticipated rise in plasma $PYY_{3-36}$ and $GLP-1_{(7-36)amide}$ concentrations using the oral $B_{12}$ uptake pathway is comparable to rates of infusion adopted within these studies.

The major advantages of this delivery system then are (1) oral delivery; (2) both GLP-1 and $PYY_{3-36}$ have previously been shown to maintain biological potency when conjugated; (3) $B_{12}$ is able to cross the blood-brain barrier; (4) the quantity of peptide that is required for clinical efficacy is well within the $B_{12}$ uptake capacity.

High Benefit-risk Ratios Due to the Combination of Endogenously Released Compounds and Vitamin $B_{12}$ Ultimately, the final compound that is administered is a conjugate of $B_{12}$ and an endogenously occurring peptide. No known toxicity of vitamin $B_{12}$ has been reported, and only minimum intake recommendations are established. Moreover, the prevalence of deficiencies in Vitamin $B_{12}$ are quite common in obese and diabetic patients, indicating a possible further therapeutic role for the $B_{12}$ compound (Daousi, C. et al. 2005 *J. Clin. Endocrinol. Metab.* 90:5025-30). With respect to the endogenously occurring peptides, it seems unlikely that short-term risks may be associated with their administration, and to date, no such risks have been reported. The major perceivable risk associated with this proposed anti-obesity drug revolves around the development of a resistance to the action of the peptide over the long-term. This is unlikely to occur however, considering that this treatment will result in the administration of peptides comparable to their physiological levels only. Furthermore, since increased meal frequency (a condition expected to result in a greater release of these endogenous peptides) is associated with greater appetite control (Speechly, D. P. and R Buffenstein, 1999 *Appetite* 33:285-97), it lends support to the notion that resistance to these peptides is unlikely to occur at physiological levels (receptor expression is changed in response to acute elevations in these peptides; however "resistance" has to date not been observed).

The unique uptake pathway provides an innovative approach to delivering appetite suppressing peptides via oral ingestion by evading gastrointestinal proteolysis and increasing intestinal absorption. Peripheral administration of these compounds, at levels well within the capacity of the proposed uptake pathway, have previously been shown to demonstrate efficacious appetite suppressing properties in a variety of rodent and non-human primate models, as well as both lean and obese humans with and without Type 2 DM. An acute caloric reduction of up to 31% has been achieved with the delivery of these peptides. Given that a 10% weight-loss threshold has previously been recommended, and that current anti-obesity drugs only achieve a 5% (placebo subtracted) reduction in body-weight, it is conceivable that these peptides will be successful. As a comparison, sibutramine (one of only three FDA approved drugs for chronic weight loss) has been shown to reduce acute caloric intake by 16% in a group of obese subjects (versus the 30% observed in the study of Batterham et al. (2003 *New England J. Med.* 349:941-8) using $PYY_{3-36}$, which corresponded to a mean weight loss of 10% (Barkeling, B. et al. 2003 *Int. J. Obesity Related Metabol. Disord.* 27:693-700).

Since, current routes of study related to these peptides require repeated injections, this innovative delivery strategy then offers a novel means in which to not only deliver the peptides, but also to study the action of these peptides. In particular, since multiple injections induce stress in the animal models utilized (which has been touted as the underpinning reason for the large variations observed with $PYY_{3-36}$, our full understanding of the effects of these peptides has been impeded.

Finally, the peptides in this application are envisioned to have many therapeutic applications that are beneficial to obesity-related morbidities.

Administration

In a further embodiment of the invention there is provided a medicament which comprises a complex according to the invention together with a pharmaceutically acceptable carrier or diluent.

Administration may be oral, transdermal, buccal, by inhalation, by rectal or vaginal suppository. Administration may be by injection. Injection may be subcutaneous or intravenous. Injection may be by catheter or syringe. In preferred embodiments, administration is oral.

Examples of pharmaceutically acceptable carriers and diluents include typical carriers and diluents such as sodium bicarbonate solutions and similar diluents which neutralize stomach acid or have similar buffering capacity, glycols, oils, oil-in-water or water-in-oil emulsions, and include medicaments in the form of emulsions, gels, pastes and viscous colloidal dispersions. The medicament may be presented in capsule, tablet, slow release or elixir form or as a gel or paste. Furthermore, the medicament may be provided as a live stock feed or as food suitable for human consumption.

Pharmaceutically acceptable carriers include conventional excipients such as binders, including gelatin, pre-gelatinized starch, and the like; lubricants, such as hydrogenated vegetable oil, stearic acid and the like; diluents, such as lactose, mannose, and sucrose; disintegants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

Pharmaceutically acceptable carriers may be either solid or liquid form. Solid form preparations include powders, tablets, dispersible granules, capsules, and cachets. A solid carrier is suitably one or more substances which may also act as diluents, flavoring agents, solubilizers, lubricants, suspending agents, binders or tablet disintegrating agents. The solid carrier material also includes encapsulating material. In powders, the carrier is finely divided active compounds. In the tablet, the active compound is mixed with the carrier having the necessary binding properties in suitable proportions and compacted in the shape and size desired. Suitable solid carriers include, but are not limited, to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Delivery may use a sustained release form.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations which are intended to be converted, shortly before use, to liquid form preparations for either oral or parental administration. Such liquid forms include solutions, suspensions, and emulsions. These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric measuring device.

Pharmaceutical compositions for injection comprise appropriate physiologically acceptable carriers. A variety of aqueous carriers may be used, e.g., buffered water, saline, 0.3% glycine and the like. Stabilizers such as plant-derived glycoproteins, albumin, lipoprotein, fibronectin and/or globulin may also be added. Other components of the pharmaceutical compositions of the invention can include pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like, as well as combinations thereof. The liquid utilized will be chosen with regard to the route of administration.

In some embodiments, the conjugate is administered as a chewing gum. The conjugate may be included in a known chewing gum composition such as those described in U.S. Pat. No. 7,078,052, which is incorporated herein by reference. The chewing gum can be low or high moisture, sugar or sugarless, wax containing or wax free, low calorie (via high base or low calorie bulking agents), and/or may contain dental agents.

Chewing gum generally consists of a water insoluble gum base, a water soluble portion, and flavor. The water soluble portion contains the conjugate and optionally flavor and dissipates with a portion of the conjugate over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35%, by weight, of the chewing gum.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients.

Embodiments of the invention provide a method of delivering an active substance to any uni- or multicellular organism, including bacteria, protozoa, or parasites, which has a requirement for Vitamin $B_{12}$ as well as a specific uptake mechanism for the same, which method comprises administering a complex of the invention to the organism.

EXAMPLE 1

Vitamin $B_{12}$ as a Carrier for the Oral Delivery of Insulin

Vitamin $B_{12}$ mediated insulin delivery was systematically investigated. The results on the synthesis, characterization and purification of a novel $B_{12}$-insulin conjugate with hypoglycemic properties as tested in vivo in STZ-induced diabetic rats are presented below.

Figure 2:
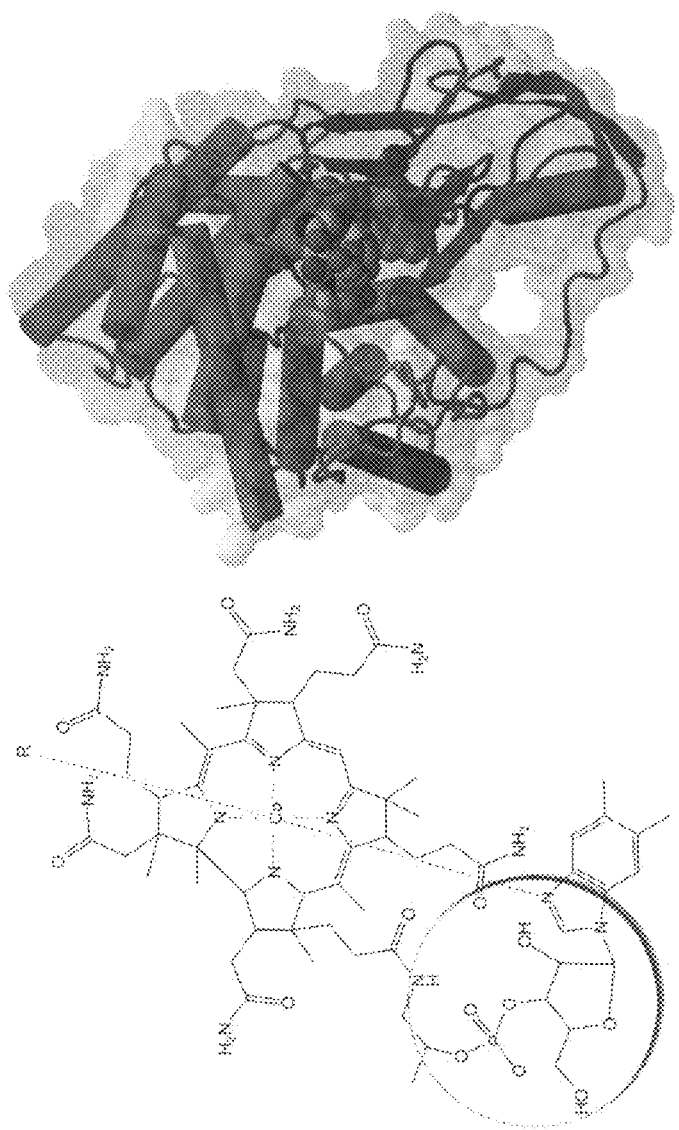
FIG. 2. The structure of Vitamin $B_{12}$ (left) and the binding pocket of $B_{12}$ in the TCII/$B_{12}$ complex with the solvent-accessible fragment of the $B_{12}$ molecule visible. This is also shown on the left, circled.

Bovine insulin was directly conjugated using CDI, on the B strand at lysine29 (K29), to the 5'-hydroxyl group of the α-ligand of $B_{12}$ to provide a carbamate linked conjugate. Coupling of insulin through the $B_{12}$ 5'-OH ribose group was performed because previous work had established that coupling at this position did not interfere with recognition by $B_{12}$ uptake proteins (G. J. Russell-Jones et al. 1995 *Bioconjugate Chem.* 6:34-42; H.P.C. Hogenkamp et al. in *Chemistry and Biochemistry of $B_{12}$* (R. Banerjee), Wiley, New York, 1999, pp. 385-410; A. M. Mitchell et al., in *Enzymatic Mechanisms* Vol. 27 (P. A. Frey and D. B. Northrop), Ios Press, Amsterdam, 1999, pp. 150-154). The reason for this is illustrated in FIG. 2 for $B_{12}$ interaction with transcobalamin II (TCII). The $B_{12}$ ribose unit is clearly solvent accessible and not involved in key recognition interactions. Studies on insulin conjugates and key residues involved in insulin receptor interactions offered several positions, particularly on the B-strand, where conjugation could be performed. LysineB29 was chosen for ease of synthesis (the only two other ε-amines (both N-termini) can be readily selectively protected for example) and because it was known to be important for insulin oligomerization but not activity (the insulin monomer is considered the active species in vivo).

Despite modification at this point it is worth noting that experiments performed in any buffer containing high concentrations of divalent cations or with high ionic strength (such as phosphate buffered saline) still resulted in significant insulin polydispersity. This polydispersity was consistent with the presence of insulin oligomer formation (dimer and hexamer) as confirmed by velocity ultracentrifugation and $C_{18}$ Reverse phase HPLC. These oligomers can aggregate and precipitate and also greatly hinder purification of the desired $B_{12}$-insulin conjugate. Mutation or modification of residues in the C-terminal region of the B strand of insulin, especially the $Thr^{B27}$, $Pro^{B28}$ or $Lys^{B29}$ positions, has a dramatic effect on insulin association, greatly reducing dimer and hexamer formation. Given that $B_{12}$ is conjugated to insulin at LysB29 oligomer formation likely proceeds through a process other than the antiparallel beta strand formation between two insulin C-terminal regions. This is likely zinc based interactions with residues such as HistidineB10. Conjugation to the C-terminal region does not appear to prevent oligomerization, and conditions that promote such oligomerization are preferably avoided to obtain, in a facile manner, the desired $B_{12}$-insulin conjugate. This is preferably achieved in low molarity, chelex washed HEPES containing EDTA.

Figure 3:
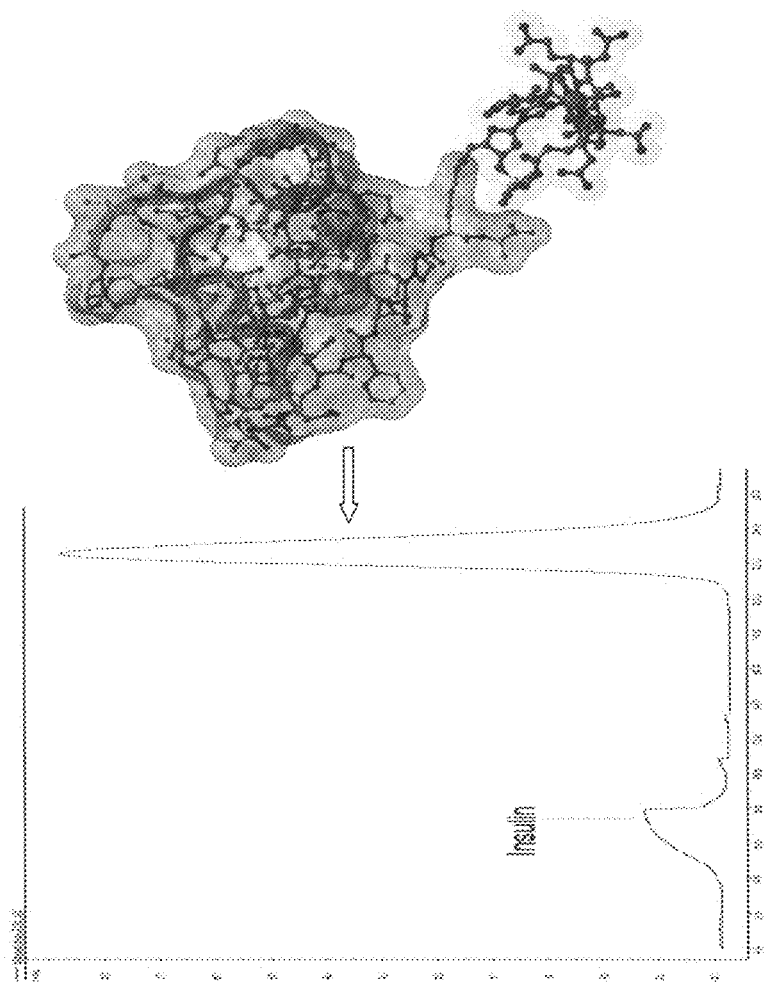
FIG. 3. Anion-exchange (DEAE) chromatogram showing separation of insulin from insulin-$B_{12}$ conjugate. The structure of insulin-$B_{12}$ conjugate is shown with coupling of $B_{12}$ and insulin at the 5'-ribose-OH and lysineB29 residue respectively.

Coupling was attempted at pH's ranging from 6.8 to 9.7 using coupling agents such as CDI and 1,1'-carbonyldi(1,2,4-triazole). CDI proved the most successful especially when used in large excess (3 to 5-fold relative to $B_{12}$). More alkaline pH produced better conjugation results but prolonged exposure to such a high pH resulted in precipitation, presumably due to insulin aggregation or deamination. As a result, upon completion of coupling at pH 9.7, dialysis was performed in 50 mM HEPES at pH 6.8 to both remove impurities such as CDI and unreacted $B_{12}$, but also to bring the pH into a region where these problems are minimized. Purification was achieved by dialysis to remove reagents under 3,500 molecular weight, followed by anion-exchange chromatography to remove residual, unconjugated, insulin (FIG. 3).

Figure 4A:
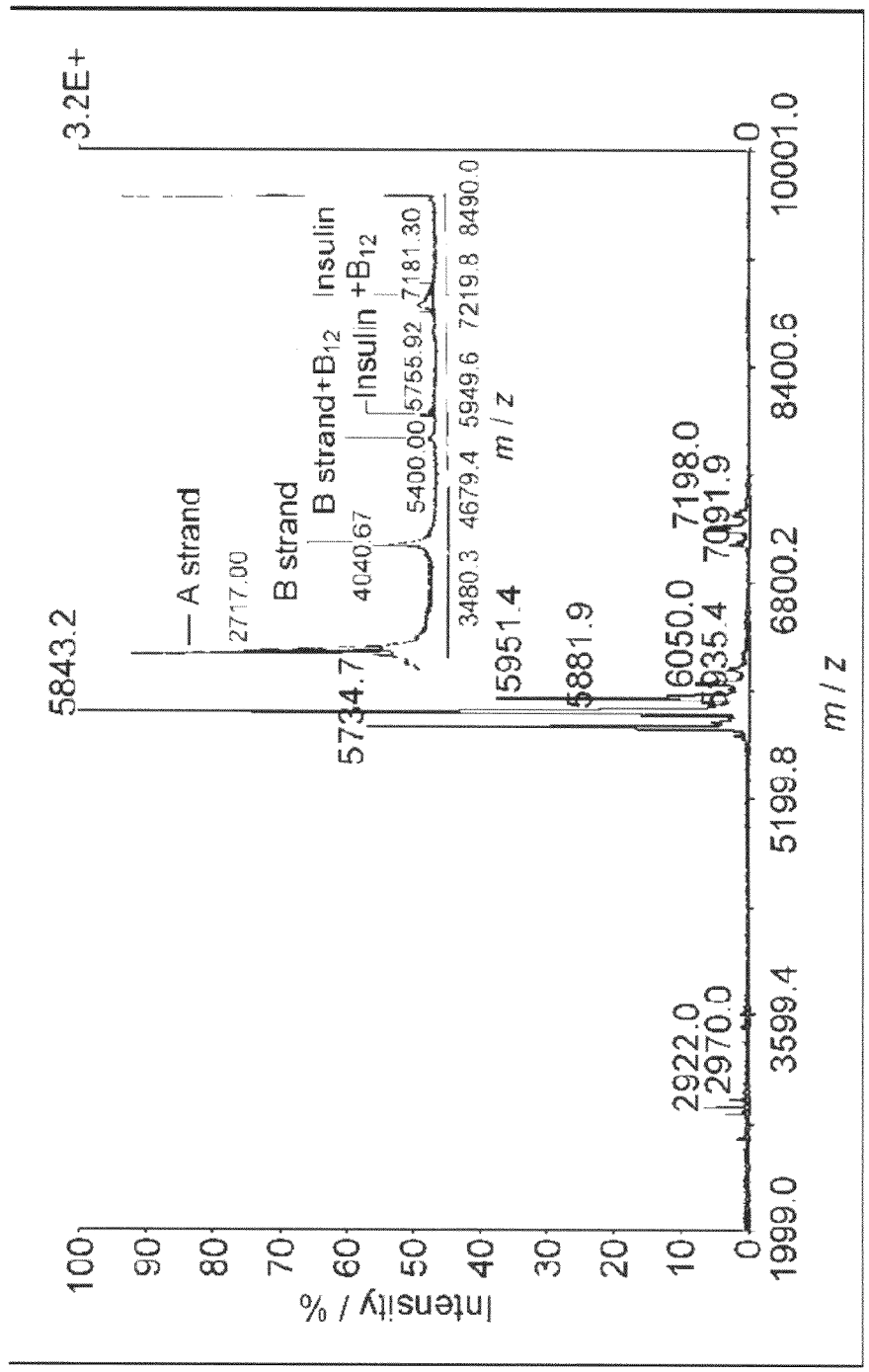
FIG. 4. (a) MALDI-TOF MS of insulin-$B_{12}$ conjugate: Data for $B_{12}$-insulin in matrix containing no DTT and 10 mM ODTT (inset). ODTT reduces the disulfide links between both insulin strands. Both traces show a mix of "free" insulin control and $B_{12}$-insulin conjugate: (m/z): (M+) for free insulin at 5734, 1 at 7091.9; with 10 mM DTT (m/z): (M+) insulin A strand at 2717.00, B strand at 4040.67, B strand+$B_{12}$ at 5400.00, insulin at 5755.92 and insulin+$B_{12}$ at 7181.30. Note the presence of $B_{12}$ bound only to the insulin B strand with no A strand-$B_{12}$ observed. (b) Circular dichroism melting experiments at 222 nm showing $B_{12}$-insulin. Result is consistent with folded insulin (helical nature can be seen in FIG. 2). (c) Velocity ultracentrifugation plot showing single species, indicative of monomeric $B_{12}$-insulin.
Figure 4B:
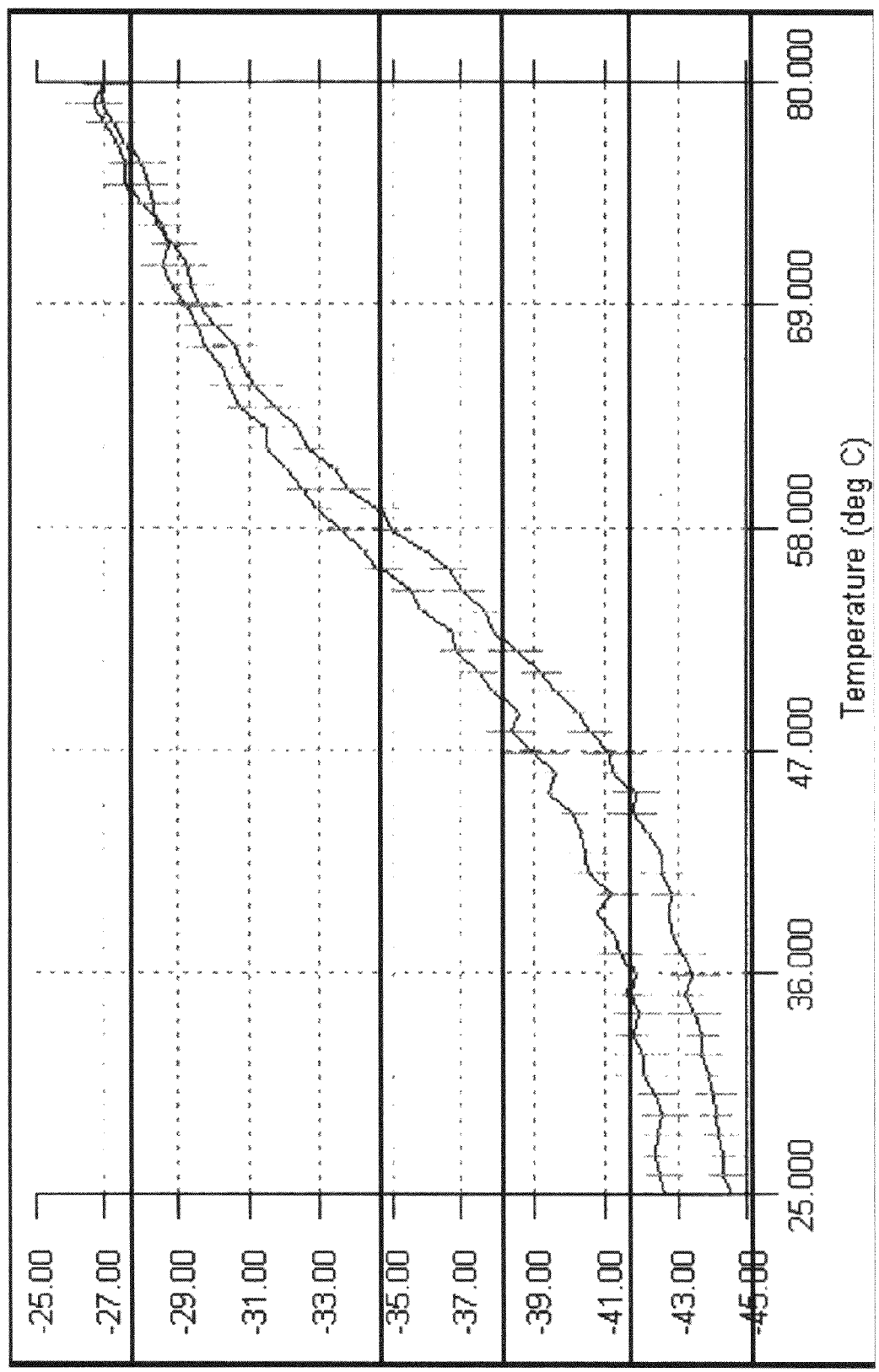
Figure 4C:
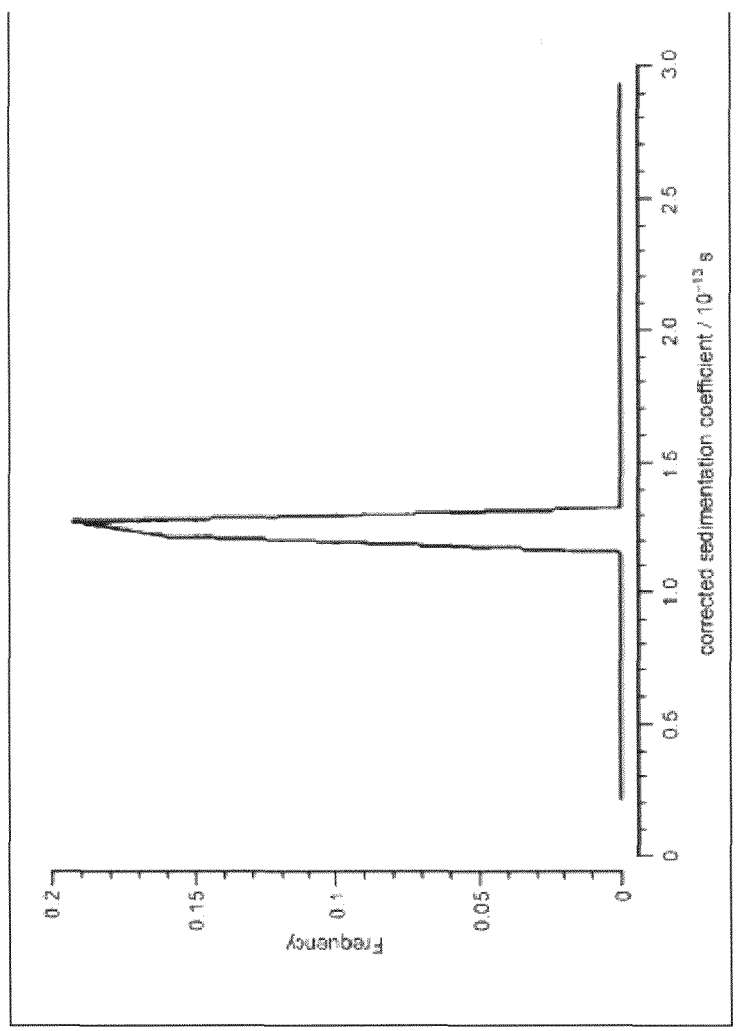

Data for $B_{12}$-insulin in matrix containing no DTT and 10 mm ODTT are shown in FIG. 4a (inset). ODTT reduces the disulfide links between both insulin strands. Both traces show a mix of "free" insulin control and $B_{12}$-insulin conjugate: (m/z): (M+) for free insulin at 5734, 1 at 7091.9; with 10 mm DTT (m/z): (M+) insulin A strand at 2717.00, B strand at 4040.67, B strand+$B_{12}$ at 5400.00, insulin at 5755.92 and insulin+$B_{12}$ at 7181.30. Note the presence of $B_{12}$ bound only to the insulin B strand with no A strand–$B_{12}$ observed. (b) Circular dichroism melting experiments at 222 nm showing $B_{12}$-insulin. Result is consistent with folded insulin (helical nature can be seen in FIG. 2). (c) Velocity ultracentrifugation plot showing single species, indicative of monomeric $B_{12}$-insulin.

Figure 5:
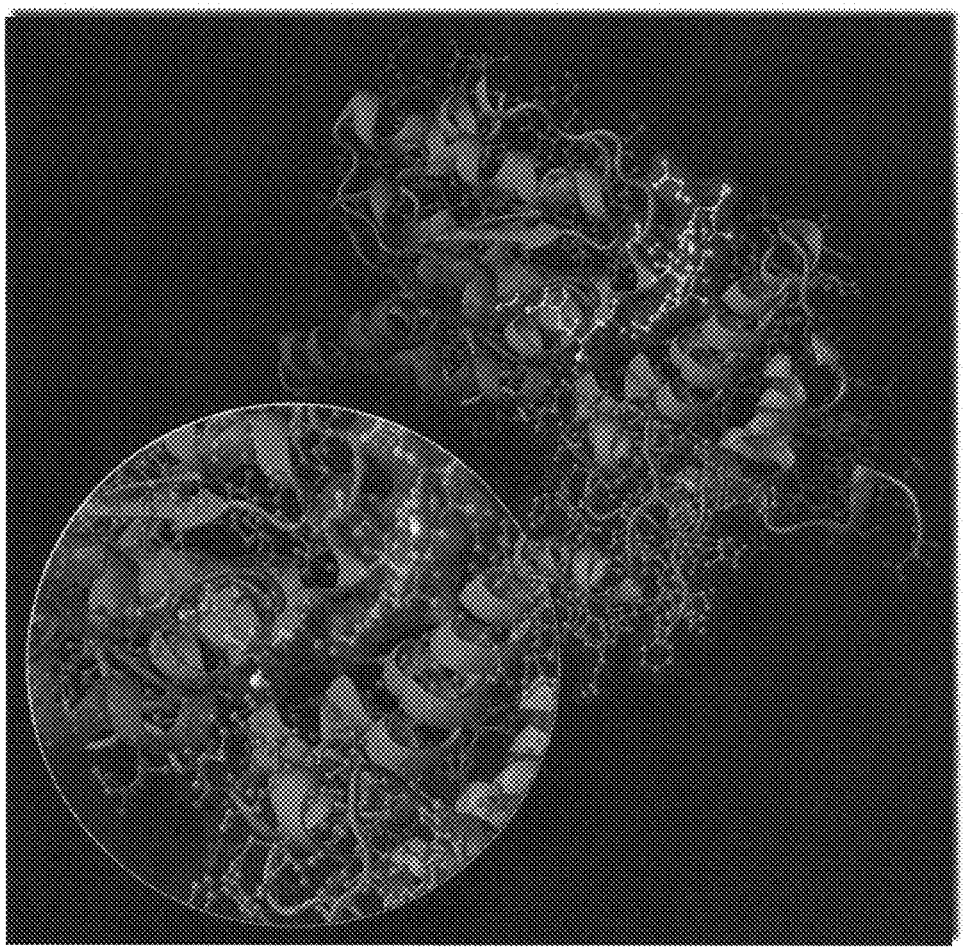
FIG. 5. The bases for this structure can be found in the Protein Data Bank, including the TCII-$B_{12}$ complex reported in PDB entry 2BB5 (the only hack in the structure calculation involved the replacement of the cobalt for iron to use already available bond parameters) and the insulin structure reported in PDB entry 1ZNI. The covalent attachment of the insulin to $B_{12}$ is described below. Structure manipulation was performed with a combination of NanoEngineer-1 and VMD, VMD being included in the mix in order to generate the ribbon renderings of the insulin and TCII protein backbones. As for the accuracy of the calculation, time and a synchrotron X-ray source will tell. The picture shows an orally active, glucose-lowering vitamin $B_{12}$-insulin conjugate bound to the $B_{12}$ uptake protein transcobalamin II (TCII). The inset shows a close-up view of the TCII binding pocket. (Insulin is in red; vitamin $B_{12}$ is in bright yellow.)

With reference to FIG. 5, the bases for this structure can be found in the Protein Data Bank, including the TCII-$B_{12}$ complex reported in PDB entry 2BB5 (the only hack in the structure calculation involved the replacement of the cobalt for iron to use already available bond parameters) and the insulin structure reported in PDB entry 1ZNI. The covalent attachment of the insulin to $B_{12}$ is described below. Structure manipulation was performed with a combination of NanoEngineer-1 and VMD, VMD being included in the mix in order to generate the ribbon renderings of the insulin and TCII protein backbones. As for the accuracy of the calculation, time and a synchrotron X-ray source will tell. The picture shows an orally active, glucose-lowering vitamin $B_{12}$-insulin conjugate bound to the $B_{12}$ uptake protein transcobalamin II (TCII). The inset shows a close-up view of the TCII binding pocket. (Insulin is in red; vitamin $B_{12}$ is in bright yellow.)

Figure 6:
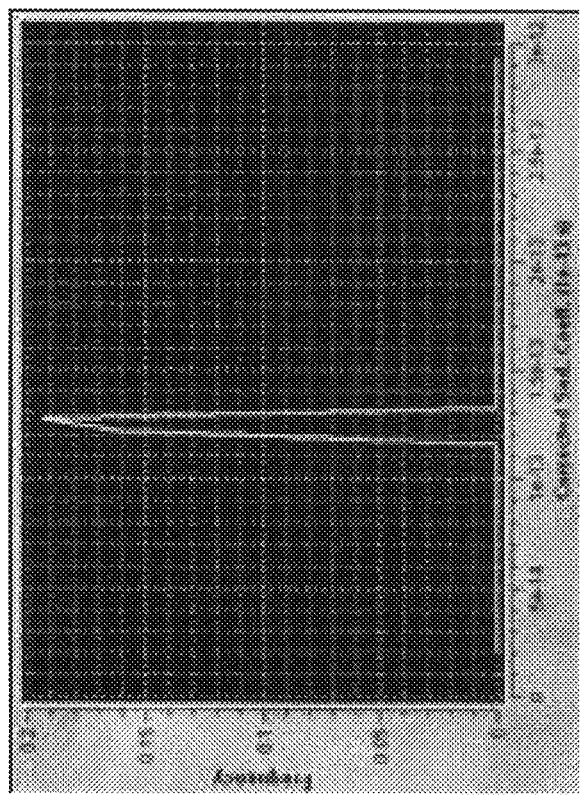
FIG. 6. Velocity ultracentrifugation plot for purified insulin-$B_{12}$ conjugate in 50 mM HEPES buffer, run at 40,000 rpm at 10° C. and monitored at 270 nm. Sedimentation coefficient is $1.285 \times 10^{-13}$ s.

Velocity ultracentrifugation experiments were performed to verify the presence of only one species in the final purified sample (FIG. 6). The species had an average molecular weight at 270 nm of ~7,000 g/mol (1 weighs ~7,200 g/mol) calculated from the experimentally derived sedimentation coefficient of $1.29 \times 10^{-13}$ s. This is comparable with literature values of $1.25 \times 10^{-13}$, $1.65 \times 10^{-13}$ and $1.84 \times 10^{-13}$ s for the insulin monomer (5733 g/mol), dimer (11466 g/mol) and hexamer (34,398 g/mol), respectively (S. Kunze et al. 2004 *Chem. Int. Edit.* 43:5025-9). This indicates a new, monodisperse sample has been obtained.

Figure 7:
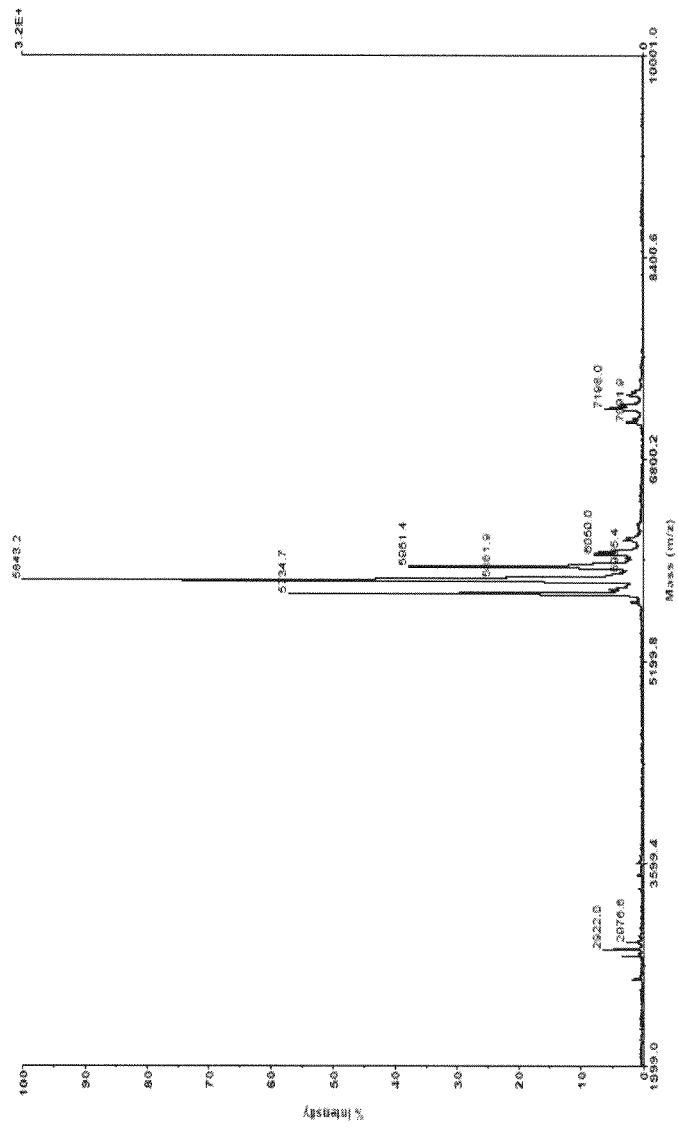
FIG. 7. MALDI-TOF mass spectra of insulin-$B_{12}$ conjugate. MALDI-TOF mass spectrometry on $B_{12}$-insulin in matrix containing no dithiothreitol (DTT) and (inset) (10 mM) DTT. DTT reduces the disulfide links between both insulin strands. Both figures show a mix of 'free' insulin control and $B_{12}$-insulin conjugate. (m/z): (M+) for free insulin at 5734, insulin-$B_{12}$ conjugate at 7091.9; With 10 mM DTT (m/z): (M+) insulin A strand at 2717.00, B strand at 4040.67, B strand+$B_{12}$ at 5400.00, insulin at 5755.92 and insulin+$B_{12}$ at 7181.30. Note the presence of $B_{12}$ bound only to the Insulin B-strand with no A-strand–$B_{12}$ observed.

MALDI-TOF Mass spectrometry experiments in matrix with and without the reducing agent dithiothreitol (DTT) established that the desired conjugate had been synthesized and that the $B_{12}$ is not conjugated to insulin on the A strand, which would have indicated failed protection of the terminal amines (FIG. 7). No multiple conjugates (e.g. 2:1 $B_{12}$ to insulin) were observed by MALDI-TOF or SDS-PAGE electrophoresis. This was further supported by velocity ultracentrifugation experiments.

Melting temperature circular dichroism studies (222 nm) confirm the insulin is still folded, resulting in a melting temperature at ~65° C. similar to unconjugated insulin controls. Electronic absorption analysis shows maxima consistent with both the presence of $B_{12}$ and insulin and the peak at 361 nm (ε of 27,500 M−1 $cm^{-1}$) was used to calculate solution concentration (A. O. Hill et al. 1965 *J. Chem. Soc.* 46:2859-65). The $B_{12}$-insulin conjugate has been prepared at concentrations up to (27 μM). Spectrophotometric Intrinsic Factor (IF) in vitro binding studies confirm that the key enzyme in the $B_{12}$ uptake pathway is recognizing the $B_{12}$-insulin conjugate.

Figure 8A:
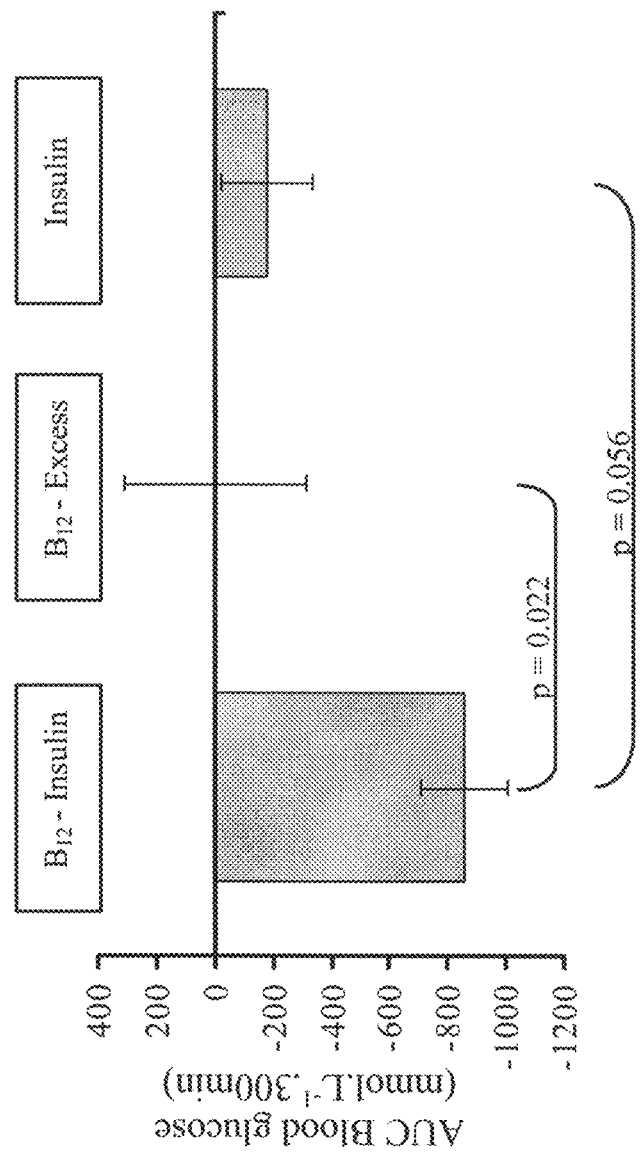
FIG. 8. Blood glucose response following administration of either the $B_{12}$-insulin conjugate (n=7); $B_{12}$-insulin dissolved in $10^5$-fold excess $B_{12}$ (n=4); or free insulin (n=5). (a) Percent change in blood glucose in response to the administration of the three treatments in the STZ-induced diabetic rat model. Asterisk represent a significant difference (p<0.05) from the pre-administration value (0 min time-point) for the $B_{12}$-insulin conjugate only. (b) Represents the area under the blood glucose curve following administration of the three treatments. Area under the curve is expressed as $mmol.L^{-1}.300$ min. Error bars represent S.E.M.
Figure 8B:
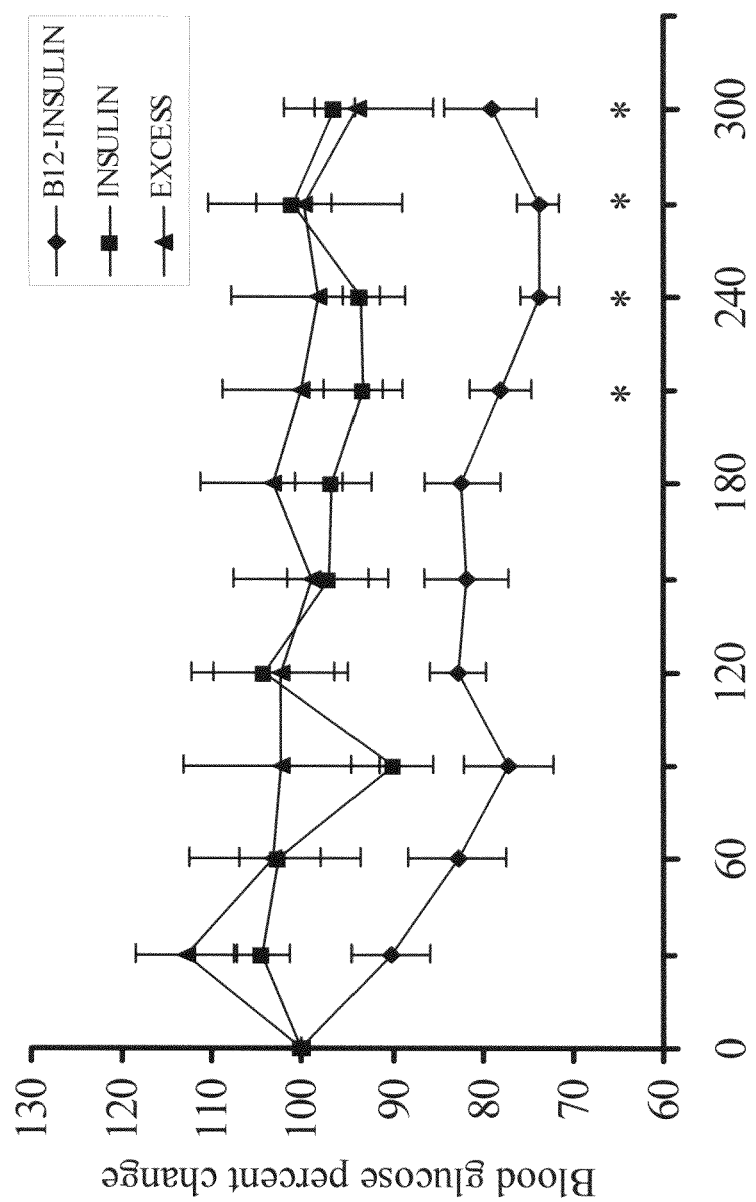
Figure 9:
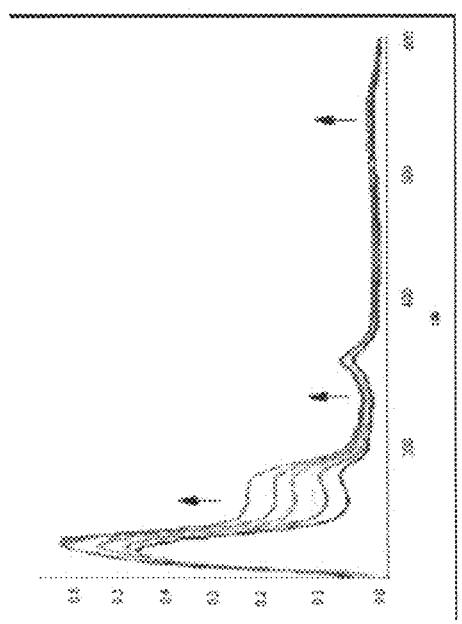
FIG. 9. Intrinsic Factor binding studies showing successful binding of insulin-$B_{12}$ conjugate to Intrinsic Factor, a key protein in $B_{12}$ uptake (R. H. Allen et al. 1973 *J. Biol. Chem.* 248:3670).
Figure 10:
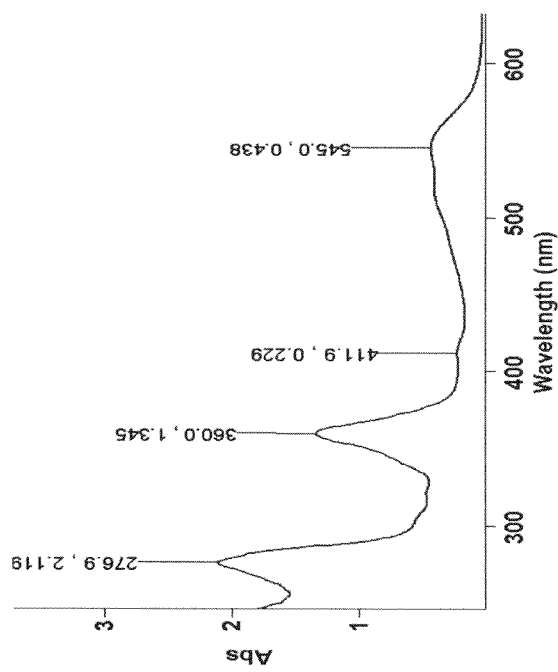
FIG. 10. Electronic absorption spectra of insulin-$B_{12}$ conjugate.
Figure 11:
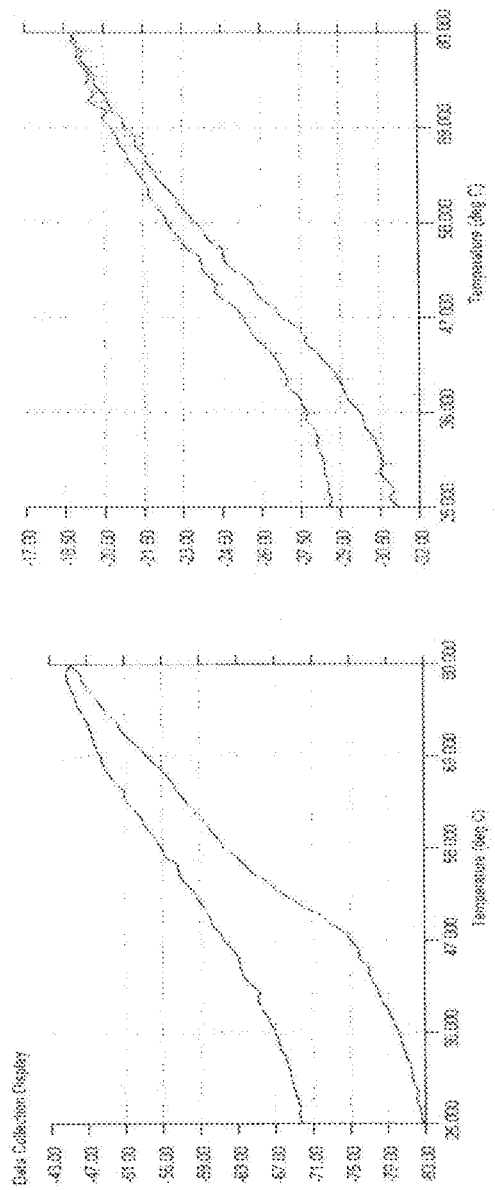
FIG. 11. Melting Circular Dichroism (Y-axis=Molar ellipticity) (a) Free insulin. (b) insulin-$B_{12}$ conjugate.
Figure 12:
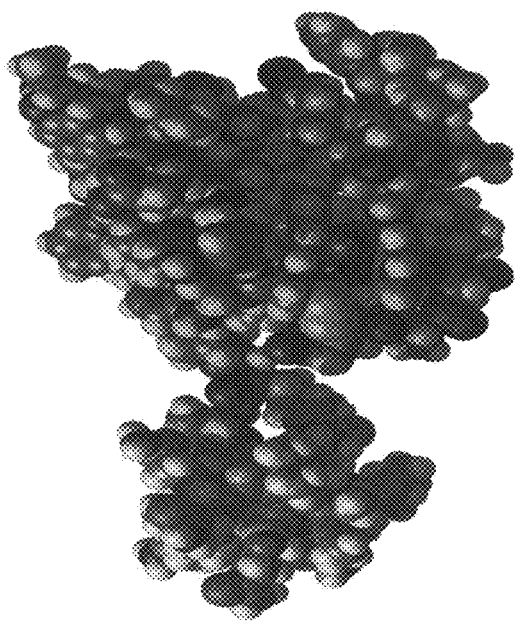
FIG. 12. Space fill representation of the $B_{12}$-insulin conjugate. Key residues involved in both $B_{12}$ recognition and insulin receptor binding are not affected by the conjugation according to model studies (N. L. Allinger 1977 *J. Am. Chem. Soc.* 99:8127-8134; W. Humphrey, et al. 1996 *J. Mol. Graph.* 14:27-28.
Figure 13A:
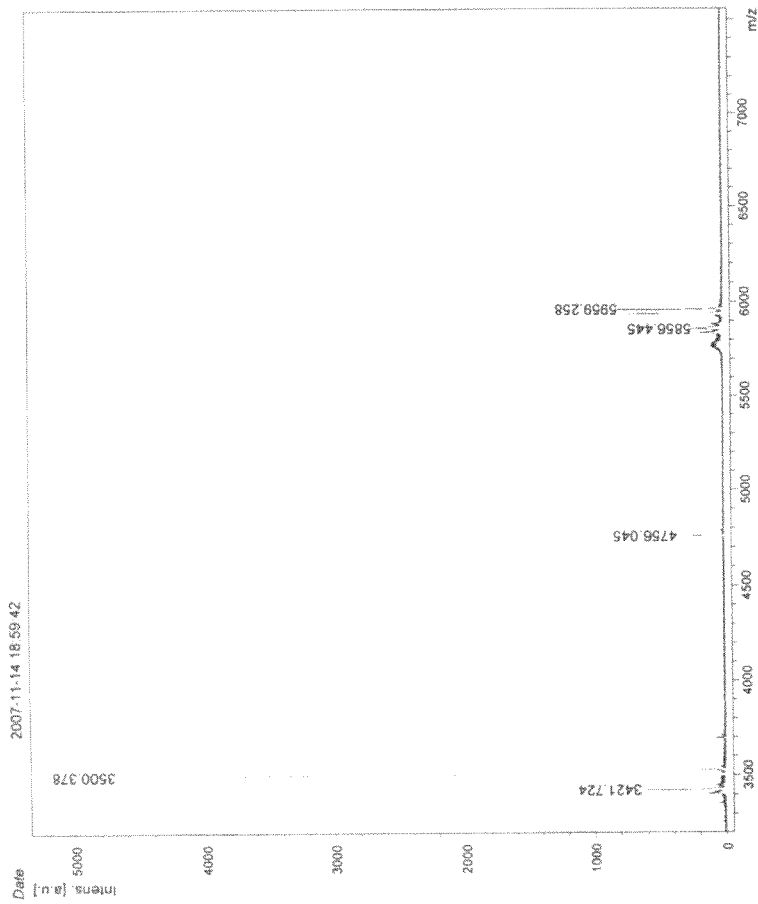
FIG. 13. (A) AKP1 MALDI with CDT coupling, with DTT. (B) AKP1 CDT synthesis MALDI, no DTT. (C) AKP1 with CDT coupling FPLC separation.
Figure 13B:
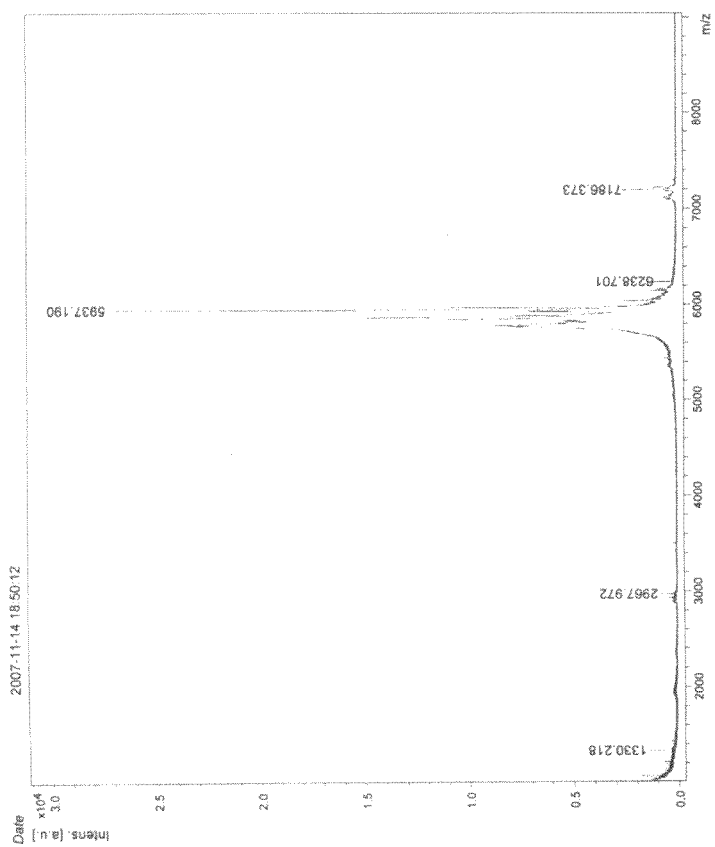
Figure 13C:
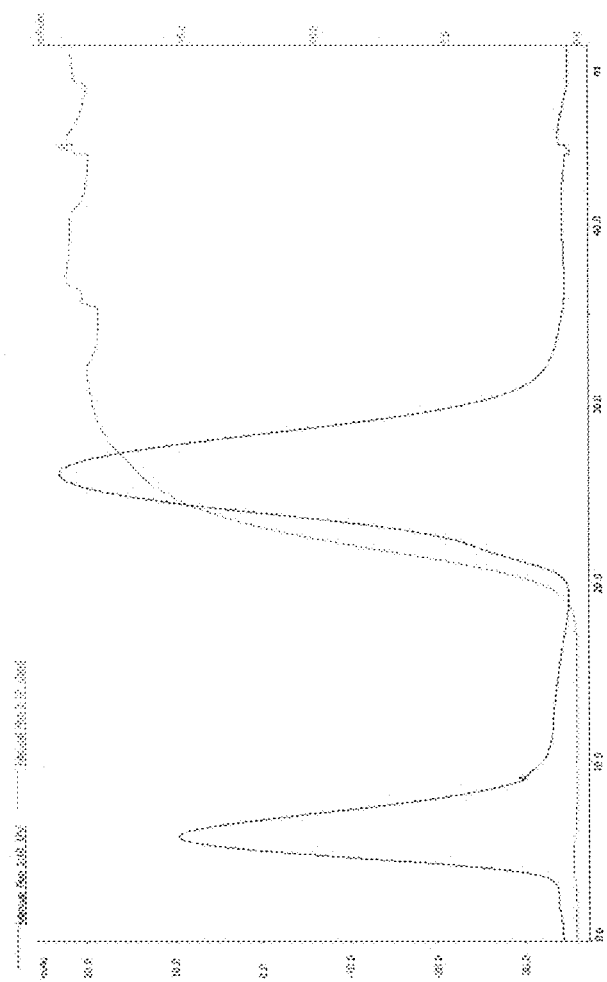
Figure 14:
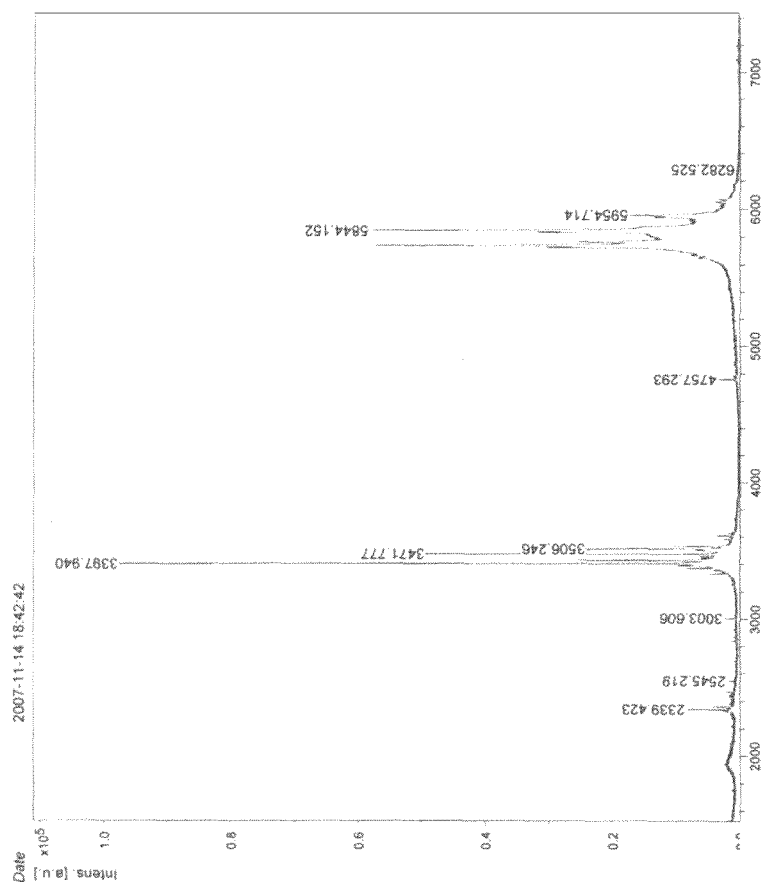
FIG. 14. AKP3 MALDI with DTT.
Figure 15:
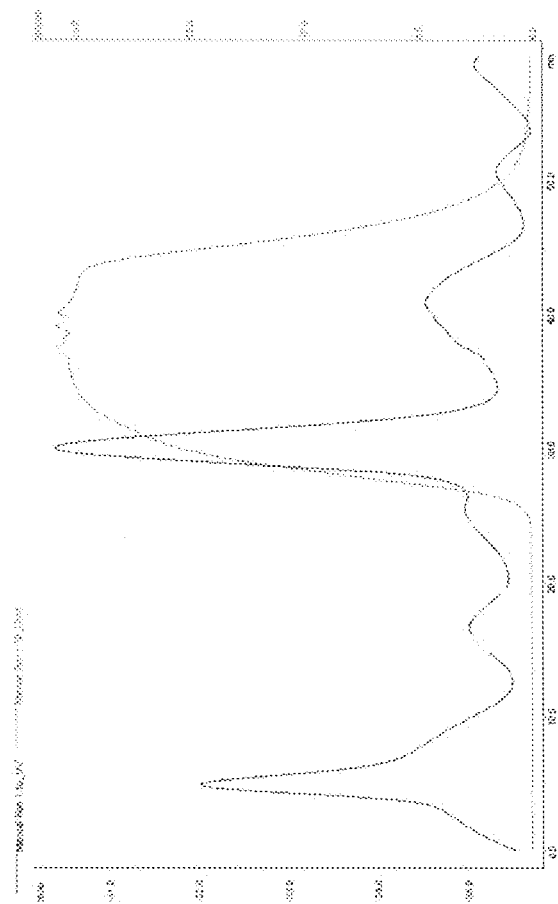
FIG. 15. AKP3 anion exchange chromatography.
Figure 16:
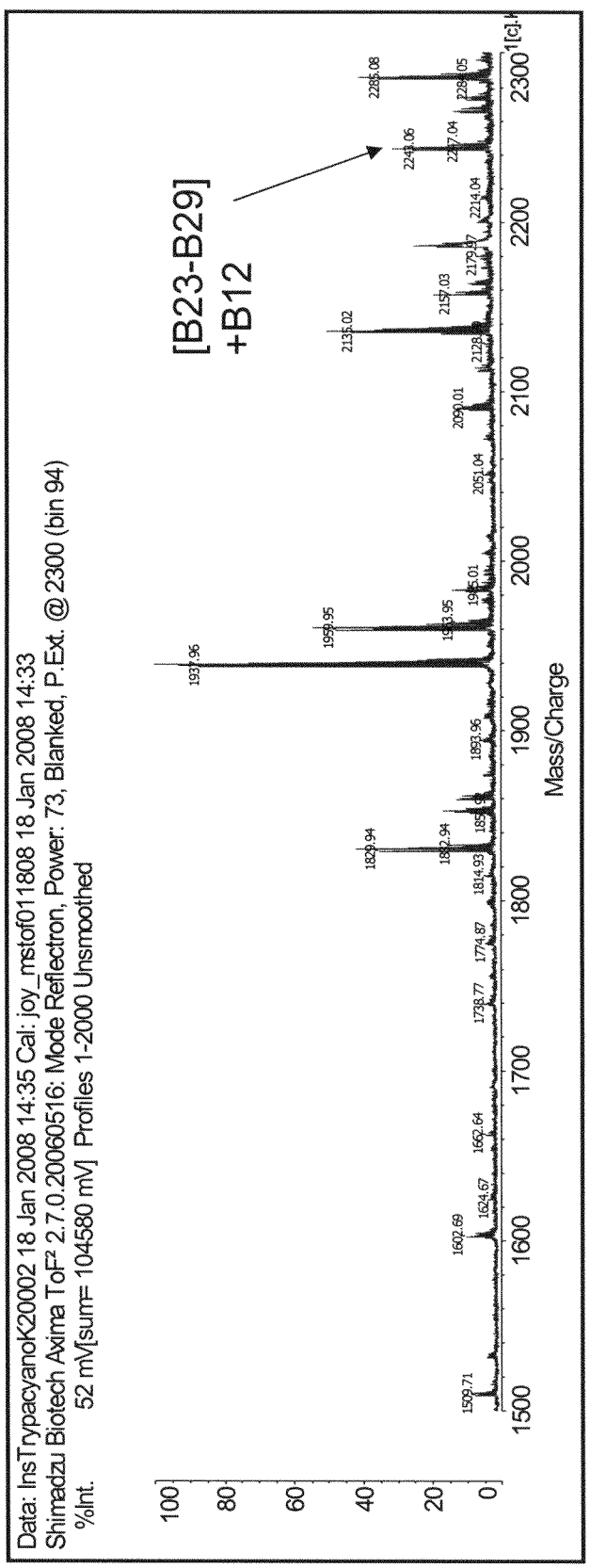
FIG. 16 shows that the vitamin $B_{12}$ has been coupled to the lysine at position 29 on the insulin B strand.

To examine the in vivo efficacy of the $B_{12}$-insulin conjugate, blood from the STZ-induced diabetic rat model was sampled by means of a jugular catheter prior to and subsequent to oral administration of the $B_{12}$-insulin conjugate and compared to the blood glucose response following administration of an equimolar solution of free insulin (FIG. 8A and B).

Prior to administration of compounds via oral gavage, fasting (>4 h) blood glucose levels confirmed that rats were hyperglycemic (15.6±0.8 mmol/L; ±SEM) indicating that an insulin-deficient state had been achieved.

Results identified that the $B_{12}$-insulin conjugate was associated with a 4.7-fold greater decrease in the area under the blood glucose curve (p=0.056) when compared to the blood glucose response to the administration of free insulin. To identify whether the corresponding change in blood glucose concentration was mediated by a $B_{12}$-dependent uptake pathway, the blood glucose concentration in response to the $B_{12}$-insulin conjugate administration was compared to the blood glucose response to an identical dose of the $B_{12}$-insulin conjugate dissolved in $10^5$-fold excess $B_{12}$ (FIGS. 8A and B). There was a significant (p=0.022) decrease in the blood glucose response when the $B_{12}$-insulin conjugate was dissolved in $10^5$-fold excess $B_{12}$. It is worth noting that the presence of excess $B_{12}$ did not result in oligomerization of the conjugate as followed by analytical HPLC.

Results obtained from the oral administration of the $B_{12}$-insulin conjugate indicate that the conjugate is more effective than free insulin in reducing blood glucose levels (FIGS. 8A and B). Furthermore, when compared to results obtained in the $B_{12}$-excess trials, it is clear that the glucose lowering effects of the $B_{12}$-insulin conjugate are mediated by the $B_{12}$ uptake mechanism. The nadir in the blood glucose response in the present study occurred at 4 h which is consistent with previous pharmacokinetic experiments with orally administered radiolabelled-$B_{12}$ (J. D. Bagnato et al. 2004 *J. Org. Chem.* 69:8987-96).

Given that excessive blood sampling may stimulate the release of catecholamines, the experiments were terminated by 5 h post administration. However, based on the blood glucose response curve it is very likely that the hypoglycemic activity of the $B_{12}$-insulin conjugate could extend beyond the 5 h recording phase adopted in the present study. This is most likely due to the delayed uptake of the $B_{12}$-insulin conjugate (J. D. Bagnato et al. 2004 *J. Org. Chem.* 69:8987-96), but an extended half-life of the $B_{12}$-insulin conjugate when compared to native insulin (10 min) (F. Tietze et al. 1953 *J. Am. Chem. Soc.* 75:1758-1760), similar to transferrin (Tf)-bound conjugates (J. Alsenz et al. 2000 *Pharm. Res.* 17:825-32) cannot be ruled out.

The most remarkable and unexpected finding of the present study was the hypoglycemic response to the oral administration of the $B_{12}$-insulin conjugate and its dependence on the $B_{12}$ uptake mechanism. However, it must be noted that the $B_{12}$ uptake capacity in humans is limited to approximately 1-2 μg per dosage and as such, the amount of peptide that can be introduced through the $B_{12}$ pathway is limited (J. A. Robertson et al. 1985 *Gastroenterology* 88:908-912). This limitation could be counteracted by multiple dosing (ileal IF receptors recycle every 30 minutes) (S. Kanazawa et al. 1983 *Lancet* 1:707-8) or by conjugating multiple insulin molecules to $B_{12}$. Indeed, the conjugation of multiple insulin molecules is a likely therapeutic preference given the versatility of this system that will allow for extensive modifications with conjugation at different insulin residues, at different $B_{12}$ sites (both designed to minimize disturbance of uptake and receptor recognition) and through linkers of various lengths; with the ultimate aim of optimizing the uptake versus activity relationship between $B_{12}$ and insulin for greatest activity and in vivo residency.

In conclusion, the improved ease associated with the non-invasive delivery of insulin is likely to yield stricter control of blood glucose levels and better clinical outcomes in individuals with DM. Here we present an oral insulin delivery mechanism that has proven in vivo efficacy, is highly adaptive from a chemistry viewpoint and presents potential future clinical relevance as part of a non-invasive basal/bolus insulin therapy.

Reagents and chemicals. All reactions were done under dinitrogen atmosphere unless otherwise stated. Vitamin $B_{12}$ (Cyanocobalamin), bovine insulin, trifluoroacetic acid, dimethyl sulfoxide (DMSO), carbonyldiimidazole (CDI), 4-(2-Hydroxyethyl)piperazine-1-ethanesulfonic acid (HEPES), sodium carbonate, ethylenediaminetetraacetic acid (EDTA), triethyl acetic acid (TEA), dimethyl maleic anhydride (DMMA), CHELEX and sinapinic acid were purchased from Sigma-Aldrich. Intrinsic Factor (IF) was purchased from MD Biomedicals. HEPES buffer was washed in CHELEX resin (15 g per liter of buffer) to remove any divalent metal ions that may promote insulin aggregation. Diethyl Ether was purchased from Sigma-Aldrich and dried in a standard still. DMSO was dried over 4 Å molecular sieves (200-400 mesh, Sigma). Methanol and acetonitrile were chromatography grade and purchased from Sigma-Aldrich. Hydrochloric acid (12 M) and sodium chloride were purchased from Fisher Scientific. Dithiothreitol (DTT) was purchased from EMD Chemicals. Dialysis tubing was purchased from Pierce with 3,500 and 7,000 MWCO. SDS-PAGE gels were prepared by standard literature procedures (J. Sambrook and D. Russell D in *Molecular Cloning* (Cold Spring Harbor Laboratory Press, Cold Spring Harbor), 2001, Vol. 3, pp. A8 pt43}. Water was distilled and deionised to 18.6 MΩ using a Barnstead Diamond Reverse Osmosis machined coupled to a Barnstead Nano Diamond ultrapurification machine. MALDI-TOF mass spectrometry was performed on Applied Biosystems Voyager-DE with a laser intensity of 3922 Hz. The MALDI matrix was 10 mg sinapinic acid dissolved in a 40:60 methanol:acetonitrile mixture with 0.001% TFA with and without (10 mM) DTT. Insulin was used as a control (5733 m/z) to account for variance common with MALDI-TOF mass spectrometry (W. C. Chang et al. 2007 *Analytica Chim. Acta*, 582:1-9). An Agilent 1100 HPLC with manual injection and automated fraction collector was fitted with a Zorbax $C_{18}$ analytical column for purification. Electrospray mass spectrometry was in HEPES buffer performed on a Schimadzu LCMS-2010 A system at a cone voltage of 70 kV as 50 μL samples. All preparatory centrifugation was done at 4000 rpm, at 4° C. for 10 min using a Sorvall Centrifuge with swinging rotor.

DMMA protection of insulin. The protection of insulin has previously been reported (N. J. Kavimandan et al. 2006 *Bioconjugate Chem.* 17:1376-84). This procedure, slightly modified, is as follows. Insulin (25 mg, 4.3 μmol) was dissolved in 5 mL of 50 mM HEPES buffer with 25 mM EDTA. The pH was adjusted to be within the range of 6.8-6.9 with 1 M sodium carbonate. A three-fold molar excess of dimethylmaleic anhydride (DMMA) (5 mg, 43 μmol) was dissolved in 1 mL of DMSO. One third of the DMMA was added to the insulin and the pH was adjusted back to 6.8-6.9 with 1 M HCl. The insulin was slowly rotated at 4° C. for 30 minutes. The pH was checked at the end of the 30 minutes and adjusted as before. The remaining two thirds of the DMMA solution were then added in the same fashion. The pH was again checked to be between 6.8-6.9 and the solution allowed to rotate at 4° C.

over night. The protected insulin was dialyzed, with gentle stirring at 4° C., against 50 mM HEPES buffer with 25 mM EDTA. One liter of buffer was changed every three-five hours for a total of four liters of buffer.

Activation of $B_{12}$ and reaction with protected insulin. A two-fold molar excess of $B_{12}$ (12 mg, 8.6 μmol) relative to insulin (4.3 μM), was dissolved in 2 mL of DMSO. A five-fold molar excess, compared to $B_{12}$ of CDI (3.5 mg/ml, 21.5 μmol) in DMSO was added to the $B_{12}$ solution. The reaction was rotated at 35° C. for 2 hr. The solution was then removed and triturated with 10 mL of dry ether and centrifuged. The solution was decanted and the solid washed with dry ether. The DMMA protected insulin solution obtained was then adjusted to a pH of 9.7 with 1 M sodium carbonate. The activated $B_{12}$ was added to the protected insulin and rotated at 4° C. over night. The reaction was then dialyzed against 1 L volumes of HEPES buffer pH 7.4 until the external buffer became clear. At this point, the internal solution remained pink. Bringing the pH back down to 7.4 is important here to avoid insulin aggregation and/or deamination, which can occur at higher alkaline pH over prolonged periods. To test for the presence of residual $B_{12}$ each liter of dialysis buffer was reduced to 1 mL in vacuo and electronic absorption spectroscopy and electrospray mass spectrometry was performed. Once the presence of $B_{12}$ was no longer observed (typically after 4×1 L changes) the pink solution remaining inside the dialysis tubing was then used for subsequent experiments. UV/vis: λ 360.0 nm, 411.9 nm, 545.0 nm, all concentrations calculated using $\epsilon_{360.0}$=27,291; MALDI-TOF MS (m/z): ($M^+$) for free insulin at 5734, $B_{12}$ conjugated to insulin at 7091.9; CD: $T_{melt}$ 55° C. Reactions run with 25 mg (4.4 mmol) bovine insulin typically yielded 25 μM 5 mL solutions of $B_{12}$-insulin. Yield (~3% based on Insulin). $B_{12}$ and insulin used can be recovered and utilized in subsequent conjugations.

Ion exchange separation of insulin and $B_{12}$-insulin. Ion exchange chromatography to remove and reclaim residual, unreacted insulin was performed on a GE Akta Prime Plus system. A HiTrap 5 mL DEAE FF was loaded with 2.5 mL of dialyzed reaction. Unreacted insulin eluted with 100% water with a red fraction of 1 eluting with 50% 0.5 M NaCl. SDS-PAGE electrophoresis confirmed the presence of insulin and the fraction was characterized via MALDI-TOF mass spectrometry and ultracentrifugation to verify a single species corresponding to $B_{12}$-insulin.

Gel electrophoresis. SDS-PAGE was performed using a Bio-Rad Mini Cell at 45 mA. 20 μl of sample were mixed with 20 μl of 1% SDS with 0.2 M mercaptoethanol, boiled for three minutes and run on 12.5% resolving acrylamide gel with 4% stacking gel. Protein was visualized by Coomassie blue staining.

MALDI-TOF mass spectrometry studies in the presence of DTT. DTT (10 mM) was reacted with an equivalent volume of $B_{12}$-insulin for 20 minutes and 1 μL of this combination was prepared in the aforementioned MALDI procedure. MALDI-TOF MS (m/z): ($M^+$) insulin A strand at 2717.00, B strand at 4040.67, B strand+$B_{12}$ at 5400.00, insulin at 5755.92 and insulin+$B_{12}$ at 7181.30.

Ultracentrifugation studies. Ultracentrifugation was carried out on a Beckman-Coulter Optima TLX 120,000 rpm ultracentrifuge. Velocity studies were conducted at 40,000 rpm at 10° C. at 270 nm. A two-chamber cell with quartz lenses was loaded with 450 μL of HEPES buffer pH 9.7 and 400 μL of purified $B_{12}$-insulin in 50 mM HEPES at pH 9.7. Molecular weight was calculated from the sedimentation coefficient using Ultrascan version 8.0 Software for MS Windows.

Intrinsic Factor binding studies. Intrinsic Factor (10 mg, 0.23 μg) was dissolved in 1 mL $dH_2O$. A 50 μL aliquot of $B_{12}$-insulin was added to 950 μL of 50 mM HEPES buffer. Baseline was run against HEPES buffer and the first scan of $B_{12}$-insulin was taken without Intrinsic Factor. A 5 μL aliquot of Intrinsic Factor was added to the $B_{12}$-insulin, mixed and a second scan was taken. This procedure was repeated for five additions of Intrinsic Factor.

Electron absorption spectra. Samples were run on a Varian Cary 50 Bio spectrometer in a 1 mL quartz cuvette (Sigma) between 200 nm and 800 nm. Temperature control was maintained by a Peltier junction at 37° C.±0.1° C.

Melting circular dichroism (CD) studies. Circular dichroism (CD) was performed on an Aviv model 202 spectrometer set at 222 nm with a 1 mL Quartz cuvette. All samples were prepared in 50 mM HEPES buffer (pH 9.7) with 25 mM carbonate and 10 mM EDTA and heated from 25 to 80° C. in 1° increments then cooled from 80 to 25° C. in the same increment. Sample concentrations ranged from 1.00 μM to 1.35 μM. Heating over ~85° C. resulted in irreversible unfolding of both insulin and the $B_{12}$-insulin conjugate. All results were duplicated per batch and run for every batch prior to in vivo testing.

Animals. Male Sprague Dawley rats (323±36; ±SD; n=12) were purchased pre-catheterised (Jugular vein) from Charles River Laboratories (Wilmington, Mass.), acclimatised for three days and then rendered insulin-deficient via infusion of streptozotocin (STZ; 60 mg/kg body weight) dissolved in citrate buffer and used within 15 min of preparation. Blood glucose concentration was assessed over four days to ensure fasting levels of greater than 14 mmol/L (>250 mg/dl) were reached. Animals were housed individually and maintained on a 12-hr light-dark (0600-1800 h) cycle with free access to food (standard laboratory chow; Scotts' Distributing, Inc) and water. Maintenance of animals and experimental protocols were conducted in accordance with federal regulations and approved by the Syracuse University Institutional Animal Care and Use Committee (Protocol Number SU 09-102)

Animal experimental design. On the day of experimentation, animals were fasted for 4 hours prior to the sampling of blood (50 μl) and the $B_{12}$-insulin compound (100 nm/ml) was subsequently administered via oral gavage (1 ml). Blood was then sampled at 30-, 60-, 90-, 120-, 150-, 180-, 210-, 240-, 270- and 300-min after the administration of the conjugate for the calculation of area under the blood glucose curve (YSI 2300 STAT PLUS, YSI Incorporated, Yellow Springs, Ohio). Two control groups were used in this set of experiments; the first received a molar-equivalent concentration (100 nm) of free insulin (1 ml) while the second control group received the same quantity of the $B_{12}$-insulin conjugate as the experimental group, however the conjugate was dissolved in $10^5$-fold excess $B_{12}$.

Computational characterization of insulin. Energy minimization of the component systems was performed using the MM2 molecular mechanics force field (N. L. Allinger 1977 *J. Am. Chem. Soc.* 99:8127-8134). Graphics were generated using VMD (W. Humphrey, et al. 1996 *J. Mol. Graph.* 14:27-28) and POVRay (Persistence of Vision Raytracer, v.3.6.1, on WorldWide Web at: povray.org) on a 1.5 GHz processor (Powerbook G4, Apple, Inc.).

EXAMPLE 2

Synthesis of Vitamin $B_{12}$ Peptide Conjugates

In this embodiment, Vitamin $B_{12}$ and peptide are either directly conjugated or conjugated with a spacer. The "spacer" groups between the peptide and $B_{12}$ are short bifunctional alkyl chains of varying lengths (typically 3-40 atoms) that facilitate both the necessary conjugation of $B_{12}$ and peptide and also provide varying degrees of separation between the two. This is to minimize any steric effects the $B_{12}$ may have on peptide-receptor interactions.

Conjugation takes place on $B_{12}$ at three major sites: (1) the cobalamin's β axial site at the cobalt atom; (2) direct conjugation of the peptide to the peripheral corrin ring propionamide units (there are three but the ε-position avoids Intrinsic Factor uptake interference); and (3) through the 5'-hydroxy group of the ribose unit of the α "tail" of $B_{12}$. Previous research suggests that modification of these sites does not affect Intrinsic Factor and TCII affinity vital for successful uptake (Pathare, P. M. et al. 1996 Bioconjugate Chem. 7:217-32).

PYY conjugation: Tertiary structure is believed to play a key role in PYY activity with loss of helicity reducing potency. The active site has been shown to be from residues 22-36 and a systematic structure-function study conducted by Balasubramanam et al. (2000 J. Med. Chem. 43:3420-7) has demonstrated that potent activity could still be achieved with modifications to certain residues even in the active terminal region. Modification at Trp27 or Tyr36 did interfere with receptor affinity ($IC_{50}$<0.5 nM) for example. Modification of Tyrosine 36 also does interfere with activity. By mutating the sequence to run with Nle at positions 24 and 28, Trp at position 30 and Nva at residue 31 a PYY of comparable activity but with greater in vivo residency was achieved. Such a PYY is used and compared with "regular" PYY conjugates for activity and stability. CD and NMR studies of such active conjugates demonstrate how altering the core PYY structure affects the secondary and tertiary structure. When coupled to information regarding activity (e.g., no activity, selective affinity for the $Y_1$ or $Y_2$ receptor only, or equal affinity for both receptors) this offers mechanistic insight into the determination of receptor subtype selectivity. Clearly however there is much room to modify PYY without great risk of activity loss and this makes it ideal for a conjugation approach.

The effects of PYY or GLP conjugation on $B_{12}$ enzyme binding and kinetics is explored by spectroscopic means as demonstrated above but also by electron microscopy. By attaching holo-transcobalamin II (prebound to conjugate as demonstrated by spectroscopic studies) to latex minibeads or gold surfaces and incubating in the presence of liver cell suspensions, visualization of binding to cells such as the endothelial cells, Kupffer cells or hepatocytes can be visualized by scanning electron microscopy. Conducting the experiment at different temperatures (e.g., 4° C. versus 37° C.) allows such dependence to be elucidated. Internalization of the peptide-probe system predicted to occur at 37° C. is visualized by transmission electron microscopy. Successful binding and uptake can then be followed. In addition, binding specificity can be demonstrated by inhibition experiments using pre-incubation with equal and excess native TCII-$B_{12}$.

Using $^{125}$I-labeled PYY and GLP-1, prepared by commercially obtaining tri-butyl tin derivatives and subsequently reacting with Na $^{125}$I to displace the tributyltin with iodine, receptor binding studies of the free peptide versus $B_{12}$-peptide conjugates are performed against all six PYY receptor subtypes and both known GLP-1 receptors subtypes. Loss of affinity, preference for certain receptor subtype is then monitored. Such PYY or GLP studies have been conducted by groups such as that of Huang et al. using pancreatic acini cells (Huang, S. C. and M. F. Tsai 1994 Peptides 15:405-10).

GLP-1 conjugation. The histidine moiety at the N-terminus of plays a central role in GLP-1 binding to GLP-1 receptors (Kim, S. et al. 2005 Biomaterials 26:3597-3606). Loss or modification of this histidine not only greatly diminishes activity but also antagonizes the activity of GLP-1. In contrast, modification of the lysine residue (K26) does not interfere greatly with binding and so is a suitable site for irreversible conjugation, again offering the opportunity to avail of enterohepatic recirculation. The lysine residue (K34) has been debated in the literature regarding whether modification diminishes activity (Kim, S. et al. 2005 Biomaterials 26:3597-3606). Coupling at this position occurs in tandem with K26 (where the N-terminal histidine has been suitably protected) producing a conjugate containing two $B_{12}$ molecules per peptide. Any activity of this peptide will provide evidence on the importance of K34 and on the benefits, or unsuitability, of conjugation of multiple $B_{12}$'S for activity.

An alternative approach involving reversible coupling of the peptides to $B_{12}$ conjugates or use of polyethylene glycol spacers is also taken. With the reversible conjugation the $B_{12}$ still facilitates the peptide's enteric transport and uptake, but the peptide is released once the conjugate arrives in the brain. Some peptide are also released in the blood, however some of this blood-released peptide also transport across the blood brain barrier, as is the case with endogenously produced peptide. This still produces an oral delivery route for each peptide but rules out extended presence of active peptide through $B_{12}$ dependent enterohepatic circulation. A route to increase peptide mean residence time involves the use of long chain polyethylene glycol (PEG) units (750-10000 Da). Conjugates of the type $B_{12}$-$PEG_{750-1000}$-peptide is produced. It is has been extensively reported in the literature that PEG conjugates exhibit increased plasma half-lives (Shechter, Y. et al. 2005 FEBS Lett. 579:2439-44), improved resistance to proteolysis, reduced immunogenicity and antigenicity compared to parental compounds including proteins (Poindexter, G. S. et al. 2002 Bioorganic Medicinal Chem. Letters 12:379-82; van Spriel, A. B. et al. 2000 Cytokine 12:666-70; Werle, M. and A. Bemkop-Schneurch, 2006 Amino acids 30:351-67). By coupling the conjugates through bifunctional PEG units with a reversible bond (e.g., a disulfide bond sensitive to reducing agents) at the peptide-PEG junction but a more stable bond (e.g., amide) at the $B_{12}$-PEG junction tailored release is achieved. This means longer-lived peptide in vivo is transported orally.

Combined, the approaches disclosed herein involve short or long chain spacers, reversibly or irreversibly coupling, offer an extensive ability to diversify and optimize the system to produce the desired uptake, activity and in vivo residency.
Chemical and Biochemical Characterization of the Vitamin $B_{12}$-Peptide Conjugates This is achieved in an analogous approach to that demonstrated in Example 1. The complexes are characterized, where appropriate, by X-ray crystal structure determination, 10 and 20 NMR spectroscopy (COSY, NOSY), circular dichroism (CD) and CD melting experiments, electronic absorption spectroscopy, MALDI-TOF and Electrospray mass spectrometry, Infra-red spectroscopy, SDS-PAGE and amino acid analysis. These experiments confirm that the conjugates are pure, coupled correctly, allow us to calculate concentrations and ensure the peptides have remained folded through the chemical coupling procedure. They also allow us to observe and define even slight structural changes in the peptides, compared to unconjugated peptide. Combined with activity studies, this allows us to correlate structure and function. Purification is achieved by a number of routes depending on each peptide. Dialysis (using size to facilitate facile purification), reverse-phase HPLC or column chromatography (silica, amberlite, DOWEX and sephadex G-25 resins) or anion-exchange chromatography is used. The stability of the bioconjugates is studied at various pH values to reflect the condition in stomach, intestine, serum and cell. The light and thermal sensitivity of the bioconjugates is established to ensure correct handling and storage conditions. Spectrophotometric $B_{12}$ binding assays with Intrinsic Factor and TCII confirm in vitro that the conjugates recognize $B_{12}$ uptake enzymes. Conjugates that give positive binding assays for both $B_{12}$ and peptide components in a particular conjugate are then used for in vivo trials. The stability of the bioconjugates with respect to concentrations of blood serum reducing agents such as cysteine and glutathione is studied for those $B_{12}$-PEG-peptide systems coupled through a reversible disulfide bond. These studies offer information on the efficacy of the 'trigger' and combined with the $B_{12}$ and peptide receptor binding assays is used to screen for conjugates suitable for in vivo testing.

Conjugation, both reversible and irreversible, is achieved using standard organic chemistry/conjugate chemistry techniques as appropriate.

Biological and in vivo Uptake Studies with Successfully Screened Conjugates

The purpose here is to demonstrate biological activity of the conjugates characterized in the experiments described above. Experiments were conducted using male Sprague-Dawley (SD) rats obtained from Charles River Laboratories (CRL; approximately 12 weeks in age). SD rats were used due to the unique bimodal distribution that results in response to a diet relatively high in fat and energy (HE) (Levin, R E. et al. 1997 *Amer. J. Physiol.* 273:R725-30). Indeed, approximately 50% of SD rats developed diet-induced obesity (DIOSD) when placed on a HE diet and these animals are characterized by rapid weight gain (32.8 g per week) and increased food consumption (25% over two weeks; full metabolic profile is characterized in Levin, R E. et al. (1997 *Amer. J. Physiol.* 273:R725-30)). The remaining 50% of the animals (diet resistant; DRSD) do not demonstrate this increased weight gain and present with similar food consumption quantities as control animals. These animal models have been chosen on the basis that they present with disparate eating behaviors and that the DIOSD rats present with similar features to those seen in humans (as opposed to an autosomal recessive gene defect model such as the Zucker rat (Levin, R E. et al. 1997 *Amer. J. Physiol.* 273:R725-30)).

The first objective assesses uptake kinetics of each conjugate (as $B_{12}$-peptide suspended in physiological buffer) to characterize the efficiency of the biological uptake system (Study 1). The second series of studies (Studies 2-3) assesses alterations in acute (first five hours) eating behavior (specifically total water and food intake) and the effect of combined therapy (assessing the additive effect of GLP-1 and $PYY_{3-36}$).

Study 1: Assessment of the Oral Dose Response Curve to the $B_{12}$-peptide Bioconjugate Administered Via Oral Gavage in the SD Rat Twelve outbred SD rats (rats that have not been phenotypically characterized as DRSD or DIOSD) are obtained from GRL and acclimatized to their surroundings for a one-week period. The jugular vein in each rat is catheterized using the surgical services of GRL prior to shipping. Each animal is then be randomly assigned to undertake four out of the following eight trials (same time of day, 0700 h; 12 hr light-dark cycle (0600-1800 h representing the light cycle)) after a twelve hour fast and separated by at least three days; 1) 1 nmol/kg of peptide as $B_{12}$-peptide; 2) 0.5 nmol/kg of peptide as $B_{12}$-peptide; 3) 0.1 nmol/kg of peptide as $B_{12}$-peptide; 4) 0.05 nmol/kg of peptide as $B_{12}$-peptide; 5) 0.01 nmol/kg of peptide as $B_{12}$-peptide; 6) 0.05 nmol/kg of peptide as $B_{12}$-peptide; 7) 1 nmol/kg of free peptide and 1 nmol/kg of free $B_{12}$; 8) the physiological buffer (carrier) solution alone. The peptide is administered into the stomach by oral gavage, wherein the quantity of solution is identical across trials. Following this design, each trial contains data from six animals (n=6 per trial). Trial 7 and trial 8 are treated as control trials.

Blood is sampled (200 µl) pre gavage, and at 60, 120, 150, 180, 240 and 300 min thereafter (the number of time-points are chosen to ensure less than 1.5 ml of blood is sampled per testing trial) via the catheter and assayed for peptide concentration (RIA; Phoenix Pharmaceuticals, Inc.). For peptide analysis, blood is treated and assayed in accordance with the peptide-specific radioimmunoassay (RIA) kit instructions (Phoenix Pharmaceuticals, Inc.). The mean area under the curve (AUG) is calculated for each trial.

Results: Each peptide appears in the blood by 120 min post-administration and demonstrates peak-plasma-concentration ($G_{max}$) at 240 min. By 300 min post-administration, the peptide concentration has returned to baseline levels. The AUG and $C_{max}$ are the lowest during control (trial 7 and trial 8) trials (derived from endogenous secretion). A graphical evaluation of the plasma $C_{max}$ and AUG (y-axes) against dose (x-axis; concentrations in trials 1-6) curve demonstrates a non-linear increase up to a dose of 0.1 nmol/kg of peptide (trial 3), upon which further increases in concentration do not yield greater $C_{max}$ and AUG values (plateau).

An alternate approach is to administer $^{125}I$ or $^{3}H$ labeled peptides and assess radioactivity in the plasma. The advantage of this approach is the increased sensitivity of the measurement and as such, smaller samples (~75 µl) are required allowing the number of sampling points to be increased. A disadvantage of this approach being that some radioactivity is expected to appear in all trials where the peptide is administered, since peptides may undergo proteolysis within the GIT and as a result, radioactive peptide-fragments may be absorbed. However, the time-course of appearance varies greatly, wherein the intact radioactive peptide-conjugate appears later (2-5 hours after oral gavage) while the radioactive peptide-fragments appear earlier (within 2 hours). Upon subtracting the time-course (per time-interval) of radioactivity appearing in the plasma of control animals (free-peptide administration) from the radioactivity appearing in the plasma of experimental animals, the uptake of conjugated peptides is established.

Study 1 demonstrates changes in the peptide concentration (as $C_{max}$ and AUG) following the oral administration of the peptide-conjugate (versus control). It is for this reason that we have chosen to assess the concentration of these peptides using the specific peptide RIA's as the primary approach. Upon completion of testing the first batch of animals (n=3 rats; completing four trials each), the peptide concentrations is assessed.

Study 2: Determination of Food and Water Intake Following an Acute Dose of the $B_{12}$-peptide Conjugate Administered Via Oral Gavage in Both the DIOSD and DRSD.

A secondary purpose during this study is to determine whether the eating responses are different between the two animal models. The peptide concentration (as $B_{12}$-peptide) adopted during this study is dependent on results of Study 1, wherein the peptide demonstrating the greatest $C_{max}$ and AUC at the lowest dose is utilized (based on graphical evaluation; see statistical section).

Twelve DIOSD and twelve DRSD rats are acclimatized to the animal care facility for a one-week period (housed individually). On day eight, animals have their bedding removed and are fasted overnight (12 hours). Fecal matter is sporadically removed during this time period (to prevent/minimize coprophagia) and at the onset of testing. Thereafter, the peptide conjugated as $B_{12}$-peptide (quantity dependent on results from Study 1) is administered directly into the stomach by oral gavage. Thirty minutes later, the pre-weighed test food (precision pellets; TestDiet®) is placed into the center of the cage and the food pot secured to the base. A water bottle containing a known quantity of water is then suspended from the cage as usual. Food and water intake is then assessed by subtracting the post-measure from the pre-measure (as weight (g) and volume (ml) for food and water respectively). Care is taken to include partially eaten pellets in the post-measure. After three days, an identical quantity of saline (compared to $B_{12}$-peptide solution) is administered directly into the stomach by oral gavage and food and water intake measured; the treatment-order is counter-balanced. These experiments are conducted in triplicate (each animal undergoing three sets of treatments) and the mean scores recorded.

Results: The conjugated peptide causes a decrease in food consumption. In addition, the DIOSD demonstrate a similar reduction in food intake then what is observed in the DRSD rats.

Alternative approach: $^{125}I$ or $^{3}H$-labeled peptides are administered during the oral gavage. At a time-point corresponding to 10 min post $C_{max}$ (as assessed in Study 1) the animal is euthanized and tissues (blood, GIT (stomach to large intestine), liver, adipose, muscle (Gastrocnemius) and brain) sampled. The tissues are assessed for radioactivity based on standard laboratory procedure. The blood samples are assayed for peptide concentration.

The purpose of this alternative approach is to unequivocally demonstrate that the peptide had no biological effect on food consumption. This is demonstrated when no decrease in food consumption occurs, even though the peptide is present (measured by RIA and radioactivity).

Study 3: Repeat Study Two Using a Combination of the Peptides Administered Via Oral Gavage in Both the DIOSD and DRSD The study design is identical to that in Study 2, with the exception of using a combination of the peptides to assess for additive effects. The concentration delivered is one-half of the concentration of each peptide delivered in Study 2. One-half is used since the rate-limiting step to plasma appearance is the vitamin $B_{12}$ uptake path (as such an equivalent concentration of $B_{12}$ is administered in Study 2 and Study 3). The control treatment is the peptide-conjugate that demonstrates the greatest reduction in food intake during Study 2.

Results: There is an additive effect of these peptides, and their combination results in a greater reduction in food intake than the control group.

Statistical Analysis: In study 1, significant differences in plasma-peptide concentration within trials are assessed using a one-way ANOVA (trial 8 subtracted (endogenous control group); e.g. Mean plasma concentration in trial 1 at 60 min subtract mean plasma concentration in trial 8 at 60 min) with repeated measures (time). Where a significant result is demonstrated, a Tukey post Hoc analysis is conducted to identify time-points. AUC and $C_{max}$ are calculated for each trial and the differences between trials 1-7 (trial 8 subtracted (endogenous control group); e.g. AUC for trial 2 subtract the AUC for trial 8) assessed using a one-way ANOVA with repeated measures (trial). Where a significant result is demonstrated, a Tukey post Hoc analysis is conducted to identify trials (which represents peptide dose). The dose-response curve (trial 1-6) is fitted to a four-parameter logistic function using nonlinear regression routines contained within Prism (vA.01, Graph-Pad software). A plateau is defined as having occurred when no significant difference between trial 1 (the highest dose) and another trial (or multiple trials) exists (based on one-way ANOVA with Tukey post Hoc). An independent t-test with a Bonferroni correction is used to assess for differences between peptide appearance in the plasma (dependent variable: AUC for trials 1-6 (trial 8 subtracted)).

In Study 2 and 3, a two-way ANOVA (group x condition (treatment)) with repeated measures (condition) is used to assess for interactions (main effect for condition; dependent variable being food intake). A Tukey post hoc is then used to assess the interaction. In all cases, homogeneity of variance is tested and where unequal, data is analyzed by equivalent non-parametric methods (e.g., Wilcoxon). Normality of distribution is assessed (Shapiro-Wilk normality test) and additional statistical analysis completed where appropriate. Significance is accepted when $P \leq 0.05$.

Longer-term treatment and endogenous peptide release in suitable rodent models. Specifically, food and water intake, body weight and carcass composition (at the termination of the study) are assessed and compared to control animals following a 56-day supplementation period with the peptide-conjugates. The peptide-conjugate is administered via drinking water and animals allowed to eat ad libitum. This study also serves to identify changes in endogenous appetite suppression that may have resulted from the long-term supplementation by removing the peptide-conjugate from the water by day 56, and monitoring food intake for the subsequent two weeks to assess whether animals return to previous food intake quantities. Additionally changes in glycemic control ($A_{1c}$ (glycohemoglobin), glucose, insulin; fasting and postprandial) as well as fasting blood lipids and lipoprotein concentrations are assessed during longer-term studies.

EXAMPLE 3

AKP1 with CDT Coupling

Use of coupling agents, such as CDI or CDT for in this application coupling the $B_{12}$ to insulin is now the standard in chemistry, and review books exist on this topic, such as, for example Hermanson, G. "Bioconjugate Techniques", AP Press.

Bovine insulin (0.010 g, $1.74 \times 10^{-6}$ mol) was protected with a three-fold molar excess of dimethylmaleic anhydride by the previously established procedure. The protected insulin solution was then collected by precipitation in 35 mL chilled isopropyl alcohol. The resulting solid was washed in chilled isopropyl alcohol, then ether. The dried sample was then dissolved in 4 mL DMSO with 1% triethylamine. Cyanocobalamin (0.005 g, $3.69 \times 10^{-6}$ mol) was activated with 1.2 molar equivalents of CDT in 2 mL dry DMSO at room temperature for 30 minutes. The insulin solution was then added to the activated cyanocobalamin and allowed to rotate gently over night at room temperature. The resulting reaction was dialyzed against 5 L of deionized water and then purified by anion exchange chromatography.

EXAMPLE 4

AKP2 Synthesis

Cyanocobalamin (0.005 g, $3.69 \times 10^{-6}$ mol) was dissolved in 2 mL dry DMSO and activated with CDT at room temperature for 30 minutes. This was then added to O,O'-Bis(2-aminoethyl)polyethylene glycol 2,000 (0.0147 g, 7.37×10$^{-6}$ mol) and the B$_{12}$-PEG product was purified by high pressure liquid chromatography using 5 mM Phosphate buffer, pH 7, and acetonitrile. The gradient went from 20% acetonitrile to 50% acetonitrile over 20 minutes. B$_{12}$-PEG had a T$_r$ at 11 minutes and was then verified by MALDI-MS. B$_{12}$-PEG was reacted with 50 mM sodium iodoacetate with the presence of a ten-fold molar excess of sodium iodoacetate. The reaction was run in 2 mL 500 mM phosphate buffer containing 0.15 M NaCl and 5 mM EDTA, pH 8.3. This was stirred under nitrogen atmosphere at room temperature overnight. The B$_{12}$-PEG-acetate product was then dried in vacuo and activated with CDT in 2 mL dry DMSO for 30 minutes at room temperature.

Bovine insulin (0.010 g, 1.74×10$^{-6}$ mol) was protected with a three-fold molar excess of dimethylmaleic anhydride by the previously established procedure. The protected insulin solution was then collected by precipitation in 35 mL chilled isopropyl alcohol. The resulting solid was washed in chilled isopropyl alcohol, then ether. The dried sample was then dissolved in 4 mL DMSO with 1% triethylamine. The insulin solution was then added to the activated B$_{12}$-PEG-acetate and allowed to rotate gently over night at room temperature. The resulting reaction was dialyzed against 5 L of deionized water and then purified by anion exchange chromatography.

EXAMPLE 5

AKP3 Synthesis

Ditertbutyl dicarbonate (0.001 g, 5.0×10$^{-6}$ mol) was stirred with N-hydroxysuccinimide (0.0012 g, 1.0×10$^{-5}$ mol) in 500 μL dry DMSO with 200 μL TEA for one hour at room temperature. This was then added drop-wise to a rapidly stirring solution of bovine insulin (0.010 g, 1.74×10$^{-6}$ mol) via syringe over two hours, then stirred at room temperature for an additional hour. The solution was precipitated in 35 mL chilled isopropyl alcohol and collected via centrifugation. The resulting solid was washed in chilled isopropyl alcohol, then ether. The dried sample was then dissolved in 4 mL DMSO with 1% triethylamine. Cyanocobalamin (0.005g, 3.69×10$^{-6}$ mol) was activated with 1.2 molar equivalents of CDT in 2 mL dry DMSO at room temperature for 30 minutes. The insulin solution was then added to the activated cyanocobalamin and allowed to rotate gently over night at room temperature. The resulting reaction was dialyzed against 5 L of deionized water and then purified by anion exchange chromatography.

EXAMPLE 6

AKP4 Synthesis

Ditertbutyl dicarbonate (0.001 g, 5.0×10$^{-6}$ mol) was stirred with N-hydroxysuccinimide (0.0012 g, 1.0×10$^{-5}$ mol) in 500 μL dry DMSO with 200 μL TEA for one hour at room temperature. This was then added drop-wise to a rapidly stirring solution of bovine insulin (0.010 g, 1.74×10$^{-6}$ mol) via syringe over two hours, then stirred at room temperature for an additional hour. The solution was precipitated in 35 mL chilled isopropyl alcohol and collected via centrifugation. The resulting solid was washed in chilled isopropyl alcohol, then ether. The dried sample was then dissolved in 4 mL DMSO with 0.5% triethylamine.

To attach PEG to the terminal amine of the B strand, O,O'-Bis(2-aminoethyl)polyethylene glycol 2,000 was reacted with sodium iodoacetate in 2 mL 500 mM phosphate buffer containing 0.15 M NaCl and 5 mM EDTA, pH 8.3. This was stirred under nitrogen atmosphere at room temperature overnight. The PEG-acetate product was then dried in vacuo. It was rediscover in 2 mL dry DMSO and activated with CDT for 30 minutes at room temperature. The activated PEG was then added to the protected insulin and rotated at room temperature overnight. The reaction was then dialyzed with a MWCO of 3,500 against 5 L deionized water. The addition of 1% TFA served to deportment the Lees 29 amine on the B chain of insulin. After dialyzing the depredated system against 50 mM HEPES buffer, pH 6.9, the internal pH was adjusted to 6.9 and the previously established DMMA protection was carried out to protect the terminal amine located on the A strand of insulin.

Cyanocobalamin (0.005 g, 3.69×10$^{-6}$ mol) was activated with 1.2 molar equivalents of CDT in 2 mL dry DMSO at room temperature for 30 minutes. The insulin -PEG solution was then added to the activated cyanocobalamin and allowed to rotate gently over night at room temperature. The resulting reaction was dialyzed with a MWCO of 7,000 against 5 L of deionized water and then purified by anion exchange chromatography.

\* \* \*

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An oral delivery conjugate comprising vitamin $B_{12}$ coupled to a therapeutically active insulin via the LysB29 of insulin covalently attached to a mono-, di-, or tri-carboxylic acid derivative or the primary (5') hydroxyl group of the ribose moiety of vitamin $B_{12}$, the conjugate exhibiting at least 80% or more of the therapeutic activity of native insulin when the conjugate is administered orally.

2. The oral delivery conjugate of claim 1, wherein the insulin is human insulin.

3. The oral delivery conjugate of claim 1, wherein the covalent attachment is via a coupling agent.

4. The oral delivery conjugate of claim 3, wherein the coupling agent provides a carbamate-linked conjugate.

5. The oral delivery conjugate of claim 4, wherein the coupling agent is selected from the group consisting of N,N'-carbonyldiimidazole (CDI), 1,3-diisopropyl-carbodiimide (DIPC), 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates.

6. The oral delivery conjugate of claim 5, wherein the coupling agent is N,N'-carbonyldiimidazole (CDI).

7. The oral delivery conjugate of claim 3, wherein the conjugate further comprises spacer units comprising polyethylene glycol monomers.

8. A pharmaceutical composition comprising the oral delivery conjugate of claim 1 and a pharmaceutically acceptable carrier.

9. The composition of claim 8, further comprising Intrinsic Factor.

10. The composition of claim 9, wherein the Intrinsic Factor is a human Intrinsic Factor.

11. A pharmaceutical composition, comprising:
an oral delivery form of insulin comprising vitamin $B_{12}$ covalently coupled to insulin, wherein the covalent coupling is between a mono-, di-, or tri-carboxylic acid derivative or the primary (5') hydroxyl group of the ribose moiety of vitamin $B_{12}$ and LysB29 of insulin; and
a pharmaceutically acceptable carrier suitable for oral delivery, wherein the oral delivery form of insulin retains about 80% or more of the biological activity of native insulin when the oral delivery form is administered to a mammal.

12. A method for treating diabetes mellitus, comprising orally administering to a patient in need thereof an amount of the pharmaceutical composition of claim 11 sufficient to lower blood glucose concentration in said patient, thereby treating the diabetes mellitus.

13. The method of claim 12, wherein the pharmaceutical composition is in an oral delivery form selected from the group consisting of a capsule, a tablet, an emulsion, a colloidal dispersion, an elixir, a gel and a paste.

14. A kit comprising the pharmaceutical composition of claim 11 and an instruction sheet for oral administration.

* * * * *